United States Patent [19]

Claussner et al.

[11] Patent Number: 5,750,553
[45] Date of Patent: May 12, 1998

[54] OPTIONALLY SUBSTITUTED PHENYLIMIDAZOLIDINES, THEIR PREPARATION PROCESS AND INTERMEDIATES, THEIR USE AS MEDICAMENTS AND THE PHARMACEUTICAL COMPOSITIONS CONTAINING THEM

[75] Inventors: Andre Claussner, Villemomble; Francois Goubet, Paris; Jean Teutsch, Pantin, all of France

[73] Assignee: Roussel Uclaf, France

[21] Appl. No.: 669,419

[22] PCT Filed: Jan. 4, 1995

[86] PCT No.: PCT/FR95/00004

§ 371 Date: Jun. 27, 1996

§ 102(e) Date: Jun. 27, 1996

[87] PCT Pub. No.: WO95/18794

PCT Pub. Date: Jul. 13, 1995

[30] Foreign Application Priority Data

Jan. 5, 1994 [FR] France ............................. 94 00042
Sep. 6, 1994 [FR] France ............................. 94 10660

[51] Int. Cl.$^6$ .......................... A01N 43/50; C07D 233/40
[52] U.S. Cl. .................... 514/392; 548/318.5; 548/321.1
[58] Field of Search .......................... 548/318.5, 321.1; 514/392

[56] References Cited

U.S. PATENT DOCUMENTS 5,411,981 5/1995 Gaillard-Kelly et al. .............. 514/386

FOREIGN PATENT DOCUMENTS

| 0494819 | 7/1992 | European Pat. Off. . |
| 494819 | 7/1992 | European Pat. Off. . |
| 0578516 | 1/1994 | European Pat. Off. . |
| 48-8703 | 11/1973 | Japan . |

*Primary Examiner*—Mukund J. Shah
*Assistant Examiner*—Tamthom T. Ngo
*Attorney, Agent, or Firm*—Bierman, Muserlian and Lucas

[57] ABSTRACT

A compound in all possible racemic, enantiomeric and diastereoisomer forms of the formula

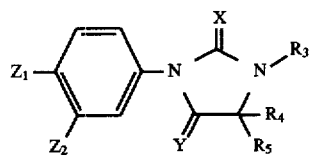

wherein Y is —O—, $Z_2$ is —$CF_3$, $Z_1$ is —CN or —$NO_2$, X is —O— or —S—, $R_3$ is hydrogen or alkyl of 1 to 4 carbon atoms optionally substituted by at least one halogen or —CN and $R_4$ and $R_5$ are individually alkyl of 1 to 4 carbon atoms optionally substituted with a member of the group consisting of halogen, —OH, esterified or etherified or protected hydroxy and phenylthio optionally substituted by halogen or —OH, and wherein at least one of $R_4$ and $R_5$ is substituted having antiandrogenic activity.

6 Claims, No Drawings

OPTIONALLY SUBSTITUTED PHENYLIMIDAZOLIDINES, THEIR PREPARATION PROCESS AND INTERMEDIATES, THEIR USE AS MEDICAMENTS AND THE PHARMACEUTICAL COMPOSITIONS CONTAINING THEM

This is a 371 application of PCT/FR 95/00004 filed on Jan. 4, 1995, published as WO95/18794 Jul. 13, 1995.

The present invention relates to new optionally substituted phenylimidazolidines, their preparation process and intermediates, their use as medicaments and the pharmaceutical compositions containing them.

In the Japanese Application J 48087030 3-phenyl 2-thiohydantoins are described which are presented as inhibiting the germination of certain plants.

In European Patent Applications 0,494,819 and 0,578,516 imidazolidines are described which are presented as possessing an anti-androgenic activity. The products of this Patent are however different from the products of the following Patent Application.

Therefore a subject of the present invention is the products of general formula (I):

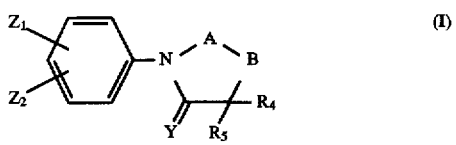

in which:

$Z_1$ and $Z_2$, identical or different, represent a cyano, nitro radical, a halogen atom, a trifluoromethyl radical or an esterified, amidified or salified free carboxy radical, the group —A—B— is chosen from the radicals

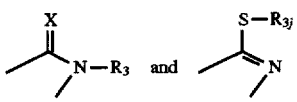

in which X represents an oxygen or sulphur atom, $R_{3j}$ represents $R_3$ with the exception of the hydrogen value and $R_3$ is chosen from the following radicals:

a hydrogen atom, alkyl, alkenyl, alkynyl, aryl or arylalkyl radicals having at most 12 carbon atoms, these radicals being optionally substituted by one or more substituents chosen from halogen atoms and the following radicals: optionally esterified, etherified or protected hydroxy, alkoxy, hydroxyalkyl, alkenyloxy, alkynyloxy, trifluoromethyl, mercapto, cyano, acyl, acyloxy, aryl, optionally substituted S-alkyl, S-aryl, in which the sulphur atom is optionally oxidized in the form of the sulphoxide or sulphone, free, esterified, amidified or salified carboxy, amino, mono- or dialkylamino, a cyclic radical containing 3 to 6 members and optionally containing one or more heteroatoms chosen from sulphur, oxygen or nitrogen atoms and the

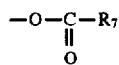

radical in which $R_7$ represents an alkyl, hydroxy, alkoxy, aryl or aryloxy radical, the alkyl, alkenyl or alkynyl radicals moreover being optionally interrupted by one or more atoms of oxygen, nitrogen or sulphur optionally oxidized in the form of the sulphoxide or sulphone, the nitrogen atoms being optionally oxidized, the aryl and aralkyl radicals moreover being optionally substituted by an alkyl, alkenyl or alkynyl, alkoxy, alkenyloxy, alkynyloxy or trifluoromethyl radical, Y represents an oxygen or sulphur atom or an NH radical, $R_4$ and $R_5$, identical or different, represent a hydrogen atom or an alkyl radical having 1 to 12 carbon atoms optionally substituted by one or more substituents chosen from halogen atoms, the

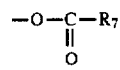

radical as defined above, the optionally esterified, etherified or protected hydroxyl radical, linear or branched phenylthio and alkylthio radicals containing at most 8 carbon atoms, phenylthio and alkylthio radicals, in which the sulphur atom can be oxidized in the form of the sulphoxide or sulphone, themselves being optionally substituted by one or more radicals chosen from halogen atoms, the optionally esterified, etherified or protected hydroxyl radical, the free, esterified, amidified or salified carboxy radical, amino, mono- or dialkylamino radicals, with the exception of the products in which $R_4$ and $R_5$, identical or different, represent a hydrogen atom or an alkyl radical having 1 to 12 carbon atoms non-substituted or substituted by one or more halogen atoms, those in which one of $R_4$ or $R_5$ represents a methyl radical and the other represents a hydroxymethyl radical, Y represents an oxygen atom or an NH radical, the group —AB— represents the radical

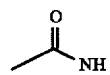

$Z_1$ in position 4 represents a nitro radical and $Z_2$ in position 3 represents a trifluoromethyl radical, those in which $Z_1$ and $Z_2$ both represent a halogen atom and those in which one of $Z_1$ and $Z_2$ represents a halogen atom, one of $R_4$ and $R_5$ represents an alkyl radical substituted by the group —S—$CH_3$ and $R_3$ represents a hydrogen atom or an alkyl radical, b) the products of formula ($I_a$)

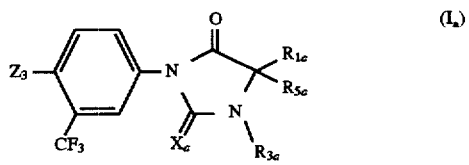

in which $Z_3$ represents a cyano or nitro radical, $R_{3a}$ represents a hydrogen atom or a linear or branched alkyl radical, containing at most 4 carbon atoms, optionally substituted by a fluorine atom, a cyano radical, $R_{4a}$ and $R_{5a}$ are such that one represents a methyl radical and the other represents a methyl radical substituted by a fluorine atom or $R_{4a}$ and $R_{5a}$ are identical and represent a methyl radical substituted by a fluorine atom, or $R_{4a}$ and $R_{5a}$ form with the carbon atom to which they are linked a cyclopentyl radical, p1 $X_a$ represents a sulphur or oxygen atom, with the exception of the product in which $Z_3$ represents a cyano radical, $X_a$ represents a sulphur atom, $R_{3a}$ represents a methyl radical and $R_{4a}$ and $R_{5a}$ form with the carbon atom to which they are linked a cyclopentyl radical, and c) the following products:
4-(4,4-dimethyl 2,5-dioxo 3-(2-fluoroethyl) 1-imidazol-idinyl) 2-(trifluoromethyl) benzonitrile,
4-(4,4-dimethyl 2,5-dioxo 3-(2,2,2-trifluoroethyl) 1-imidazolidinyl) 2-(trifluoromethyl) benzonitrile,
4-(4,4-dimethyl 3-(2-fluoroethyl) 5-oxo 2-thioxo 1-imidazolidinyl) 2-(trifluoromethyl) benzonitrile,
4-(4,4-dimethyl 2,5-dioxo 3-(2-(2-hydroxyethoxy) ethyl) 1imidazolidinyl) 2-(trifluoromethyl) benzonitrile, the said products of formula (I), (I$_a$) and the products mentioned being in all the possible racemic, enantiomeric and diastereoisomeric isomer forms, as well as the addition salts with mineral and organic acids or with mineral and organic bases of the said products.

For the definition of the substituents indicated above and in what follows, the definitions used can have the following values:

The term alkyl designates a linear or branched radical having at most 12 carbon atoms such as for example methyl, ethyl, propyl, isopropyl, butyl, isobutyl, sec-butyl, tert-butyl, pentyl, isopentyl, sec-pentyl, tert-pentyl, neo-pentyl, hexyl, isohexyl, sec-hexyl, tert-hexyl, heptyl, octyl, decyl, undecyl, dodecyl.

Alkyl radicals having at most 4 carbon atoms are preferred and notably the methyl, ethyl, propyl, isopropyl and n-butyl radicals.

The term alkenyl designates a linear or branched radical having at most 12 carbon atoms such as for example vinyl, allyl, 1-propenyl, butenyl, pentenyl, hexenyl.

Among the alkenyl radicals, the radicals having at most 4 carbon atoms are preferred and notably the allyl or butenyl radical.

The term alkynyl designates a linear or branched radical having at most 12 carbon atoms such as for example ethynyl, propargyl, butynyl, pentynyl or hexynyl.

Among the alkynyl radicals, the radicals having at most 4 carbon atoms are preferred and notably the propargyl radical.

By aryl is meant the carbocyclic aryl radicals such as phenyl or naphthyl or the monocyclic heterocyclic aryl radicals with 5 or 6 members or the heterocyclic aryl radicals constituted by condensed rings, containing one or more heteroatoms preferably chosen from oxygen, sulphur and nitrogen. Among the heterocyclic aryls with 5 members, the following radicals can be mentioned: furyl, thienyl, pyrrolyl, thiazolyl, oxazolyl, imidazolyl, thiadiazolyl, pyrazolyl, isoxazolyl, tetrazolyl.

Among the heterocyclic aryl radicals with 6 members, the pyridyl, pyrimidinyl, pyridazinyl and pyrazinyl radicals can be mentioned.

Among the condensed aryl radicals, the indolyl, benzofurannyl, benzothienyl and quinolinyl radicals can be mentioned.

The phenyl, tetrazolyl and pyridyl radicals are preferred.

By arylalkyl is meant the radicals resulting from the combination of the alkyl radicals and the aryl radicals mentioned above.

The benzyl, phenylethyl, pyridylmethyl, pyridylethyl or tetrazolylmethyl radicals are preferred.

By halogen is meant, of course, the fluorine, chlorine, bromine or iodine atoms.

The fluorine, chlorine or bromine atoms are preferred.

As particular examples of alkyl radicals substituted by one or more halogens, the following radicals can be mentioned: monofluoro, chloro, bromo or iodomethyl, difluoro, dichloro or dibromomethyl and trifluoromethyl.

As particular examples of substituted aryl or aralkyl radicals, there can be mentioned those in which the phenyl radical is substituted in the para position by a fluorine atom or by a methoxy or trifluoromethyl radical.

By acyl radical is preferably meant a radical having at most 7 carbon atoms such as the acetyl, propionyl, butyryl or benzoyl radical, but it can also represent a valeryl, hexanoyl, acryloyl, crotonoyl or carbamoyl radical: the formyl radical can also be mentioned.

By acyloxy radical is meant the radicals in which the acyl radicals have the meaning indicated above and for example the acetoxy or propionyloxy radicals.

By esterified carboxy is meant for example the radicals such as the alkyloxycarbonyl radicals, for example methoxy-carbonyl, ethoxycarbonyl, propoxycarbonyl, butyl or tert-butyloxycarbonyl.

There can also be mentioned the radicals formed with the easily cleavable ester remainders such as the methoxymethyl, ethoxymethyl radicals; the acyloxyalkyl radicals such as pivaloyloxymethyl, pivaloyloxyethyl, acetoxymethyl or acetoxyethyl; the alkyloxycarbonyloxy alkyl radicals such as the methoxycarbonyloxy methyl or ethyl radicals, the isopropyloxycarbonyloxy methyl or ethyl radicals.

A list of such ester radicals can be found for example in the European Patent EP 0,034,536.

By amidifed carboxy is meant the groups of

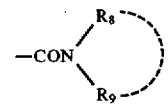

type in which the $R_8$ and $R_9$ radicals, identical or different, represent a hydrogen atom or an alkyl radical having 1 to 4 carbon atoms such as the methyl, ethyl, propyl, isopropyl, butyl, isobutyl, sec-butyl or tert-butyl radicals.

In the groups

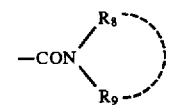

defined above, those in which the

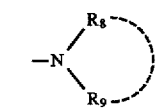

radical represents the amino, mono- or dimethylamino radical are preferred.

The

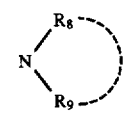

radical can also represent a heterocycle which may contain an additional heteroatom. The pyrrolyl, imidazolyl, indolyl, piperidino, morpholino, piperazinyl radicals can be mentioned. The piperidino or morpholino radicals are preferred.

By salified carboxy is meant the salts formed for example with an equivalent of sodium, potassium, lithium, calcium, magnesium or ammonium. The salts formed with the organic bases such as methylamine, propylamine, trimethylamine, diethylamine, triethylamine, can also be mentioned.

The sodium salt is preferred.

By alkylamino radical is preferably meant the radicals in which the alkyl contains at most 4 carbon atoms. The methylamino, ethylamino, propylamino or butyl (linear or branched) amino radicals can be mentioned.

Similarly, by dialkylamino radical is preferably meant the radicals in which the alkyl contains at most 4 carbon atoms. For example the dimethylamino, diethylamino, methylethylamino radicals can be mentioned.

By heterocyclic radical containing one or more heteroatoms is meant for example the saturated heterocyclic, monocyclic radicals such as the following radicals: oxirannyl, oxolannyl, dioxolannyl, pyrrolidinyl, imidazolidinyl, pyrazolidinyl, piperidyl, piperazinyl or morpholinyl.

By alkyl, alkenyl, or alkynyl radicals optionally interrupted by a heteroatom chosen from sulphur, oxygen or nitrogen atoms is meant the radicals containing one or more of these atoms, identical or different in their structure, these heteroatoms obviously not being able to be situated at the end of the radical. There can be mentioned for example the alkoxyalkyl radicals such as methoxymethyl or methoxyethyl or also the alkoxy alkoxyalkyl radicals such as methoxyethoxymethyl.

By esterified, etherified or protected hydroxyl radical is meant respectively the radicals

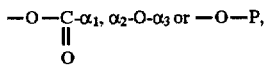

formed from a hydroxyl radical, according to the usual methods known to a man skilled in the art and in which P represents a protective group, α1, α2 and α3 represent in particular an alkyl, akenyl, alkynyl, aryl or arylalkyl radical, having at most 12 carbon atoms and optionally substituted as defined above in particular for $R_3$.

Examples of the protective group P, as well as the formation of the protected hydroxyl radical, are given in particular in the common book for a man skilled in the art: Protective Groups in Organic Synthesis, Theodora W. Greene, Harvard University, printed in 1981 by Wiley-Interscience Publishers, John Wiley & Sons.

The protective group of the hydroxyl radical that can be represented by P, can be chosen from the following list: for example formyl, acetyl, chloroacetyl, bromoacetyl, dichloroacetyl, trichloroacetyl, trifluoroacetyl, methoxyacetyl, phenoxyacetyl, benzoyl, benzoylformyl, p-nitrobenzoyl. The following groups can also be mentioned: ethoxycarbonyl, methoxycarbonyl, propoxycarbonyl, βββ-trichloroethoxycarbonyl, benzyloxycarbonyl, tert-butoxycarbonyl, 1-cyclo propylethoxycarbonyl, tetrahydro-pyrannyl, tetrahydrothiopyrannyl, methoxytetrahydropyrannyl, trityl, benzyl, 4-methoxybenzyl, benzhydryl, trichloroethyl, 1-methyl 1-methoxyethyl, phthaloyl, propionyl, butyryl, isobutyryl, valeryl, isovaleryl, oxalyl, succinyl and pivaloyl, phenylacetyl, phenylpropionyl, mesyl, chlorobenzoyl, para-nitrobenzoyl, para-tert-butylbenzoyl, caprylyl, acryloyl, methylcarbamoyl, phenylcarbamoyl, naphthylcarbamoyl.

P can in particular represent the radical

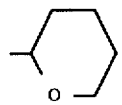

or also a silicon derivative such as trimethylsilyl.

When the products of formulae (I) and ($I_a$) as defined above contain an amino radical salifiable by an acid it is understood that these acid salts are also part of the invention. There can be mentioned the salts formed with hydrochloric or methanesulphonic acids for example.

A particular subject of the invention is the products of formula (I) as defined above, in which $Z_1$ and $Z_2$ represent a trifluoromethyl, nitro or cyano radical, Y represents an oxygen atom or an NH radical, the group —A—B— represents the radical:

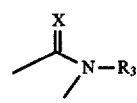

in which X represents an oxygen or sulphur atom. $R_3$ represents a hydrogen atom, a linear or branched alkyl radical containing at most 6 carbon atoms, optionally interrupted by one or more oxygen or sulphur atoms, a phenyl or pyridyl radical, these radicals being optionally substituted by one or more radicals chosen from halogen atoms, the following radicals: phenyl, optionally esterified, etherified or protected hydroxyl, alkoxy, cyano, trifluoromethyl, hydroxyalkyl, free, esterified, amidified or salified carboxy, amino, mono- or dialkylamino, the nitrogen atom of the pyridyl radical being optionally oxidized, $R_4$ and $R_5$ represent a linear or branched alkyl radical containing at most 6 carbon atoms, optionally substituted by one or more radicals chosen from optionally esterified, etherified or protected hydroxyl radicals, halogen atoms, the

radical in which $R_7$ represents a linear or branched alkyl or alkoxy radical and alkylthio and phenylthio radicals, themselves optionally substituted by one or more radicals chosen from halogen atoms and the free, esterified, etherified or protected hydroxyl radical, the said products of formula (I) being in all the possible racemic, enantiomeric and diastereoisomeric isomer forms, as well as the addition salts with mineral and organic acids or with mineral and organic bases of the said products of formula (I).

Among these products, a particular subject of the invention is the products of formula (I) as defined above, in which $Z_1$ and $Z_2$ represent a trifluoromethyl, nitro or cyano radical, Y represents an oxygen atom or an NH radical, the group —A—B— represents the group:

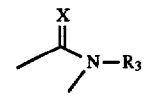

in which X represents an oxygen or sulphur atom. $R_3$ represents a hydrogen atom or an alkyl radical having 1 to 6 carbon atoms optionally substituted by one or more radicals chosen from halogen atoms and the optionally esterified, etherified or protected hydroxyl radical, the free, esterified, amidified or salified carboxy radical and the cyano radical, the alkyl radical being optionally interrupted by one or more oxygen or sulphur atoms.

$R_4$ and $R_5$ represent an alkyl radical containing at most 6 carbon atoms optionally substituted by one or more radicals chosen from the optionally esterified, etherified or protected hydroxyl radical, halogen atoms and alkylthio and phenylthio radicals themselves optionally substituted by one or more radicals chosen from halogen atoms and the hydroxyl radical, the said products of formula (I) being in all the possible racemic, enantiomeric and diastereoisomeric isomer forms, as well as the addition salts with mineral and organic acids or with mineral and organic bases of the said products of formula (I).

Among these products, a more particular subject of the invention is the products of formula (I) as defined above, in which Y represents an oxygen atom or an NH radical, $Z_2$ in position 3 represents a trifluoromethyl radical and $Z_1$ in position 4 represents a cyano or nitro radical, X represents an oxygen or sulphur atom.

$R_3$ represents a hydrogen atom or an alkyl radical having at most 4 carbon atoms, optionally substituted by one or more radicals chosen from halogen atoms or the cyano radical. $R_4$ and $R_5$, identical or different, represent a linear or branched alkyl radical containing at most 4 carbon atoms optionally substituted by a free, esterified, etherified or protected hydroxyl radical, a halogen atom, or a phenylthio radical optionally substituted by a halogen atom or a free, esterified, etherified or protected hydroxyl radical.

the said products of formula (I) being in all the possible racemic, enantiomeric and diastereoisomeric isomer forms, as well as the addition salts with mineral and organic acids or with mineral and organic bases of the said products of formula (I).

Among the preferred products of the invention, there can be mentioned more particularly the products of formula (I) as defined above the names of which follow:

2-(trifluoromethyl) 4-(4-(hydroxymethyl) 4-methyl 2,5-dioxo 1-imidazolidinyl) benzonitrile, 4-(3,4-dimethyl) 4-(hydroxymethyl) 5-oxo 2-thioxo 1-imidazolidinyl) 2-(trifluoromethyl) benzonitrile, 2-(trifluoromethyl) 4-(4-(hydroxymethyl) 3,4-dimethyl 2,5-dioxo 1-imidazolidinyl) benzonitrile, 4-(2,5-dioxo 3-(2-fluoroethyl) 4-(hydroxymethyl) 4-methyl 1-imidazolidinyl) 2-(trifluoromethyl) benzonitrile, 1,5-dimethyl 5-(hydroxymethyl) 3-(4-nitro 3-(trifluoromethyl) phenyl) 2,4-imidazolidinedione, 4-(4,4-bis(hydroxymethyl)-2,5-dioxo-1-imidazolidinyl)-2-(trifluoromethyl)-benzonitrile the said products of formula (I) being in all their racemic, enantiomeric and diastereoisomeric isomer forms, as well as the addition salts with mineral and organic acids or with mineral and organic bases of the said products of formula (I).

Also a quite particular subject of the invention is the products of formula ($I_a$) as defined above, the names of which follow:

4-(4-(fluoromethyl) 3,4-dimethyl 2,5-dioxo 1imidazolidinyl) 2-(trifluoromethyl) benzonitrile, 4-(3,4-dimethyl) 4-(fluoromethyl) 5-oxo 2-thioxo 1imidazolidinyl) 2-(trifluoromethyl) benzonitrile, 4-(2,5-dioxo 3-(2-fluoroethyl) 4-(fluoromethyl) 4-methyl 1-imidazolidinyl) 2-trifluoromethyl) benzonitrile, 4-(2,4-dioxo 1,3-diazaspiro(4.4)nonan-3-yl) 2-(trifluoromethyl) benzonitrile, 4-(2,4-dioxo 1-(2-fluoroethyl) 1,3-diazaspiro(4.4)nonan-3-yl) 2-(trifluoromethyl) benzonitrile, 1,5-dimethyl 5-(fluoromethyl) 3-(4-nitro 3-(trifluoromethyl) phenyl) 2,4-imidazolidinedione, 3-(4-cyano 3-(trifluoromethyl) phenyl) 2,4-dioxo 5-(fluoro-methyl) 5-methyl 1-imidazolidinacetonitrile, 4-(4,4-bis-(fluoromethyl) 3-methyl 5-oxo 2-thioxo 1-imidazolidinyl imidazolidinyl 2-(trifluoromethyl) benzonitrile, the said products of formula ($I_a$) being in all the possible racemic, enantiomeric and diastereoisomeric isomer forms, as well as the addition salts with mineral and organic acids or with mineral and organic bases of the said products of formula ($I_a$)

Also a subject of the invention is a preparation process for the products of formula (I), (Ia) and cited products as defined above characterized in that:

either a product of formula (II):

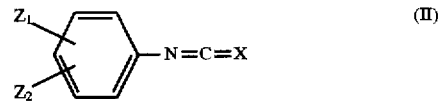

in which $Z_1$, $Z_2$ and X have the meaning indicated above, is reacted in the presence of a tertiary base with a product of formula (III):

in which $R_4$ and $R_5$ have the meaning indicated above and $R'_3$ has the values indicated above for $R_3$ in which the optional reactive functions are optionally protected and it being understood that $R_4$ and $R_5$ do not represent simultaneously a methyl radical and that if $Z_1$ represents an $NO_2$ radical in position 4, $Z_2$ represents a $CF_3$ radical in position 3, X represents an oxygen atom and $R'_3$ represents a hydrogen atom, then one of $R_4$ or $R_5$ does not represent a $CH_3$ radical and the other a $CH_2OH$ radical, in order to obtain a product of formula (IV):

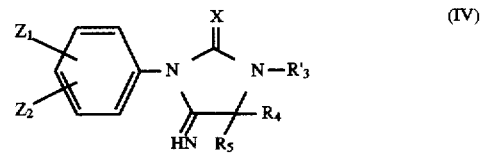

in which $Z_1$, $Z_2$, X, $R'_3$, $R_4$ and $R_5$ have the previous meaning, or the product of formula (II), as defined above, is reacted in the presence of a tertiary base with a product of formula (VII):

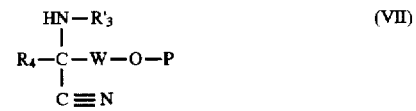

in which W has the meaning indicated above for $R_5$ with the exception of the hydrogen atom, the alkyl radical substituted by a free, esterified, etherified or protected hydroxyl radical and the value $$-O-C-R_7$$
$$\overset{O}{\|}$$

as defined above, and P represents a protective group of OH or a radical such that —O—P represents an etherified hydroxyl radical and $R'_3$ and $R_4$ have the meaning indicated above, in order to obtain a product of formula (VIII):

(VIII)

in which X, $Z_1$, $Z_2$, $R'_3$, $R_4$, W and P have the meaning indicated above, of which product of formula (VIII) if necessary and if desired, the OH radical can be released from OP which can then if necessary and if desired, be esterified or converted into a halogen radical, which products of formulae (IV) and (VIII), if necessary or if desired, are subjected to any one or more of the following reactions, in any order:

a) elimination reaction of the optional protective groups that can be carried by $R'_3$;

b) hydrolysis reaction of the >C=NH group into a carbonyl function and if appropriate conversion of the >C=S group into the >C=O group;

c) conversion reaction of the >C=O group or groups into the >C=S group;

d) action on the products of formula (IV) or (VIII) in which $R'_3$ represents a hydrogen atom, and after hydrolysis of the >C=NH group into a carbonyl function, of a reagent of formula Hal—$R''_3$ in which $R''_3$ has the values of $R'_3$ with the exception of the hydrogen value and Hal represents a halogen atom, in order to obtain products of formulae (I), ($I_a$) and cited products as defined above, in which the —A—B— group represents the group in which $R''_3$ has the meaning indicated previously then, if desired, action on these products, of an elimination agent of the optional protective groups that can be carried by $R''_3$ or if appropriate, action of an esterification, amidification or salification agent, or a product of formula (II) as defined above is reacted in the presence of a tertiary base with a product of formula (III')

$$\begin{array}{c} HN-R'_3 \\ | \\ R_4-C-R_5 \\ | \\ COOQ \end{array}$$ (III')

in which $R'_3$, $R_4$ and $R_5$ have the meaning indicated above and Q represents either an alkali metal atom or an alkyl radical containing 1 to 6 carbon atoms, in order to obtain a product of formula (IVa):

(IVa)

in which X, $Z_1$, $Z_2$, $R'_3$, $R_4$ and $R_5$ have the meaning indicated above, which if desired is subjected to any one or more of the following reactions, in any order:

a) elimination reaction of the optional protective groups that can be carried by $R'_3$;

b) conversion reaction of the >C=O group or groups into the >C=S group or if appropriate of the >C=S group into the >C=O group;

c) action on the products of formula (IVa) in which $R'_3$ represents a hydrogen atom of a reagent of formula Hal—$R''_3$ in which $R''_3$ has the values of $R'_3$ with the exception of the hydrogen value and Hal represents a halogen atom, in order to obtain products of formulae (I), (Ia) and cited products as defined above, in which the A—B— group represents the group in which $R''_3$ has the meaning indicated previously then, if desired, action on these products of an elimination agent of the optional protective groups that can be carried by $R''_3$ or if appropriate, action of an esterification, amidification or salification agent, or a reagent of formula Hal—$R''_3$ in which Hal and $R''_3$ have the values indicated previously is reacted on a product of formula (IV'):

(IV')

in order to obtain a product of formula (IV''):

(IV'')

which product of formula (IV), (IVa), (IV'), (IV'') or (VIII) represents or does not represent a product of formula (I) and which, in order to obtain if necessary or if desired a product of formula (I), is subjected to any one or more of the following reactions in any order:

a) elimination reaction of the optional protective groups that can be carried by $R''_3$ then if appropriate action of an esterification, amidification or salification agent;

b) conversion reaction of the >C=O group or groups into >C=S groups, the said products of formula (I) thus obtained being in all the possible racemic, enantiomeric and diastereoisomeric isomer forms.

The action of the products of formula (II) with the products of formula (III) is preferably carried out in an organic solvent such as tetrahydrofuran or dichloroethane but ethyl ether or isopropyl ether can also be used.

The operation is carried out in the presence of a tertiary base such as triethylamine or also pyridine or methylethylpyridine.

The optional reactive functions that can be contained by $R_3$ and that are optionally protected, are hydroxy or amino functions. The usual protective groups are used to protect these functions. There can be mentioned for example the following protective groups of the amino radical: tert-butyl, tert-amyl, trichloroacetyl, chloroacetyl, benzhydryl, trityl, formyl, benzyloxycarbonyl.

As protective group of the hydroxy radical there can be mentioned the radicals such as formyl, chloroacetyl, tetrahydropyrannyl, trimethylsilyl, tert-butyl dimethylsilyl.

It is well understood that the above list is not limitative and that other protective groups, for example known in the chemistry of the peptides, can be used. A list of such protective groups is found for example in the French Patent BF 2,499,995 whose content is incorporated here by way of reference.

The optional elimination reactions of the protective groups are carried out as indicated in the said Patent BF 2,499,995. The preferred method of elimination is acid hydrolysis using acids chosen from hydrochloric, benzene sulphonic or paratoluene sulphonic, formic or trifluoroacetic acids. Hydrochloric acid is preferred.

The optional hydrolysis reaction of the >C=NH group into the ketone group is also preferably carried out using an acid such as aqueous hydrochloric acid for example under reflux.

When the hydrolysis of the >C=NH group into the carbonyl group is carried out on a molecule also containing a >C=S group, this can be converted into the >C=O group. The free OH radical that can optionally be contained by $R_3$ can then be converted into the SH radical.

The conversion reaction of the >C=O group or groups into the >C=S group is carried out using the so-called Lawesson reagent of formula:

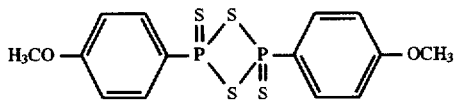

which is a product marketed for example by the FLUKA company and whose use is described for example in the publication: Bull. Soc. Chim. Belg. Vol. 87, No. 3, (1987) p. 229.

When it is desired to convert two >C=O functions into two >C=S functions the operation is carried out in the presence of an excess of Lawesson reagent. The same goes when one starts with a molecule containing a >C=S function and a >C=O function and it is desired to convert the said >C=O function into a >C=S function.

On the other hand when one starts with a molecule containing two >C=O functions and it is desired to obtain a product containing only a single >C=S function. The operation is carried out in the presence of a deficit of Lawesson reagent. Then in general a mixture of three products is obtained: each of the two products containing a >C=O function and a >C=S function and the product containing two >C=S functions. These products can then be separated by the usual methods such as chromatography.

The action on the product of formula (IV), (IVa), (IV') or (VIII) of the reagent of formula Hal—R"$_3$ is carried out in the presence of a strong base such as sodium or potassium hydride. The operation can be carried out by phase transfer reaction in the presence of quaternary ammonium salts such as tert-butyl ammonium.

The protective groups that can be carried by the R"$_3$ substituent can be for example one of those previously mentioned for $R_3$. The elimination reactions of the protective groups are carried out under the conditions indicated above.

An example of the elimination of the terbutyldimethylsilyl group by means of hydrochloric acid is given hereafter in the examples.

The optional esterification of the products of formulae (I), (Ia) and as defined above, in which R"$_3$ contains a free OH radical is carried out under standard conditions. There can be used an acid or a functional derivative, for example an anhydride such as acetic anhydride in the presence of a base such as pyridine.

The optional esterification or salification of the products of formulae (I), (Ia) and the cited products as defined above, in which R"$_3$ represents a COOH group, is carried out under standard conditions known to a man skilled in the art.

The optional amidification of the products of formulae (I), (Ia) and as defined above, in which R"$_3$ contains a COOH radical, is carried out under standard conditions. A primary or secondary amine can be used on a functional derivative of the acid for example a symmetrical or mixed anhydride.

The reaction of the product of formula (II) as defined above with the product of formula (VII) as defined above to give the product of formula (VIII) as defined above, can be carried out notably in the presence of methylene chloride at a temperature of approximately $-30°$ C.

Also a subject of the present invention is a preparation process for the products of formula (I"):

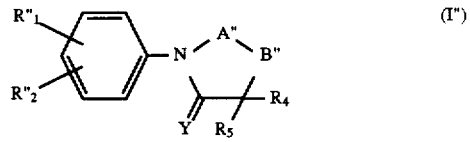

(I")

in which $R_4$ and $R_5$ are defined as above and R"$_1$, R"$_2$, —A"—B"— have the meanings indicated above for $Z_1$, $Z_2$ and —A—B—, it being understood that when —A"—B"— represents a —CO—N(R"'$_3$)— group in which R"'$_3$ represents a hydrogen atom or a linear or branched alkyl radical having at most 7 carbon atoms and Y represents an oxygen atom, R"$_1$ represents a cyano radical, process characterized in that a product of formula (V):

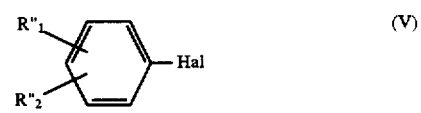

(V)

in which R"$_1$ and R"$_2$ have the previous meanings and Hal represents a halogen atom, is reacted with a product of formula (VI):

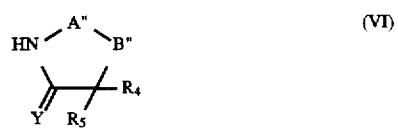

(VI)

in which —A"—B"—, $R_4$, $R_5$ and Y have the meaning indicated above, the reaction being carried out in the presence of a catalyst and optionally of a solvent.

With regard to the products of formula (V), the term Hal preferably designates the chlorine atom, but can also represent a bromine or iodine atom.

The rôle of the catalyst is probably to trap the hydrogen halide which is released and thus to facilitate the condensation reaction of the product of formula (V) with the product of formula (VI) to give the desired product.

A more particular subject of the invention is a process as defined above in which the catalyst is a metal in native or oxidized form or a base.

When the catalyst used is a metal, this metal can be copper or nickel. It can be in native form, in the form of the metal oxide or also in the form of the metal salts.

The metal salts can be a chloride or an acetate.

When the catalyst is a base, this base can be for example soda or potash and, if desired, dimethylsulphoxide can be added to the reaction medium.

A more particular subject of the invention is a process as defined above in which the catalyst is chosen from cuprous oxide, cupric oxide, copper in the native form and a base such as soda or potash.

The copper in native form used as catalyst is preferably in powdered form.

A particular subject of the invention is a process as defined above in which the catalyst is cuprous oxide.

The solvent used is preferably chosen from ethers with a high boiling point such as, for example, phenyl oxide, diglyme, triglyme and dimethylsulphoxide but can also be, for example, an oil with a high boiling point such as paraffin or vaseline.

A more particular subject of the invention is a process as defined above characterized in that the operation is carried out in the presence of a solvent of ether type such as phenyl oxide, diglyme, triglyme or dimethylsulphoxide.

A quite particular subject of the invention is a process as defined above in which the solvent used is phenyl oxide or triglyme.

The preparation process of the desired product defined above can be carried out under pressure or at atmospheric pressure, preferably at a high temperature.

Therefore a subject of the invention is a process as defined above characterized in that the reaction is carried out at a temperature higher than 100° C. and preferably higher than 150° C.

A more particular subject of the invention is a process as defined above characterized in that the reaction is carried out for more than 2 hours.

A very particular subject of the invention is a process as defined above characterized in that the reaction is carried out in the presence of cuprous oxide, in triglyme, at a temperature higher than or equal to 200° C. and for more than 3 hours.

The products which are a subject of the present invention possess useful pharmacological properties, in particular they fix on the androgen receptor and they present an antiandrogenic activity.

Tests given in the experimental part illustrate these properties.

These properties make the products of formula (I) as defined above of the present invention of use as medicaments mainly for:

the treatment of adenomas and neoplasias of the prostate as well as benign hypertrophy of the prostate, alone or in combination with analogues of LHRH. They can also be used in the treatment of benign or malignant tumours possessing androgen receptors and more particularly cancers of the breast, skin, ovaries, bladder, lymphatic system, kidney and liver, the treatment of cutaneous affections such as acne, hyperseborrhea, alopecia or hirsutism. These products can therefore be used in dermatology alone or in combination with antibiotics such as derivatives of azelaic and fusidic acids, erythromycin, as well as derivatives of retinoic acid or an inhibitor of 5α-reductase such as (5α, 17β)-1,1-dimethylethyl 3-oxo 4-aza-androst-1-ene 17-carboxamide (or Finasteride, Merck 11th Ed.) for the treatment of acne, alopecia or hirsutism. They can also be combined with a product stimulating hair growth such as Minoxidil for the treatment of alopecia.

The products of formulae (I), ($I_a$) and the cited products as defined above, in radioactive form (tritium, carbon 14, iodine 125 or fluorine 18) can also be used as a specific marker for the androgen receptors. They can also be used in diagnostics in medical imaging.

The products of formulae (I), ($I_a$) and the cited products as defined above can also be used in the veterinary domain for the treatment of behavioural disorders such as aggressiveness, androgen-dependent affections, such as circum analum in dogs, and tumours having androgen receptors. They can also be used to bring about a chemical castration in animals.

Therefore a subject of the invention is the use, as medicaments, of the pharmaceutically acceptable products of formulae (I) and ($I_a$) as defined above.

Also a subject of the invention is the use, as medicaments, of the following products:
4-(4,4-dimethyl 2,5-dioxo 3-(2-fluoroethyl) 1-imidazolidinyl) 2-(trifluoromethyl) benzonitrile,
4-(4,4-dimethyl 2,5-dioxo 3-(2,2,2-trifluoroethyl) 1-imidazolidinyl) 2-(trifluoromethyl) benzonitrile,
4-(4,4-dimethyl 3-(2-fluoroethyl) 5-oxo 2-thioxo 1-imidazolidinyl) 2-(trifluoromethyl) benzonitrile,
4-(4,4-dimethyl 2,5-dioxo 3-(2-(2-hydroxyethoxy) ethyl) 1-imidazolidinyl 2-(trifluoromethyl) benzonitrile.

A particular subject of the invention is the use, as medicaments, of the following products:
2-(trifluoromethyl) 4-(4-(hydroxymethyl) 4-methyl 2,5-dioxo 1-imidazolidinyl) benzonitrile,
4-(3,4-dimethyl) 4-(hydroxymethyl) 5-oxo 2-thioxo 1-imidazolidinyl) 2-(trifluoromethyl) benzonitrile,
2-(trifluoromethyl) 4-(4-(hydroxymethyl) 3,4-dimethyl 2,5-dioxo 1-imidazolidinyl) benzonitrile,
4-(2,5-dioxo 3-(2-fluoroethyl) 4-(hydroxymnethyl) 4-methyl 1-imidazolidinyl) 2-(trifluoromethyl) benzonitrile,
1,5-dimethyl 5-(hydroxymethyl) 3-(4-nitro 3-(trifluoromethyl) phenyl) 2,4-imidazolidinedione,
4-(4,4-bis (hydroxymethyl) 2,5-dioxo 1-imidazolidinyl) 2-(trifluoromethyl) benzonitrile.

Also a particular subject of the invention is the use, as medicaments, of the following products of formula ($I_a$):
4-(4-(fluoromethyl) 3,4-dimethyl) 2,5-dioxo 1-imidazolidinyl) 2-(trifluoromethyl) benzonitrile,
4-(3,4-dimethyl) 4-(fluoromethyl) 5-oxo 2-thioxo 1-imidazolidinyl) 2-(trifluoromethyl) benzonitrile,
4-(2,5-dioxo 3-(2-fluoroethyl) 4-(4-(fluoromethyl) 4-methyl 1-imidazolidinyl) 2-(trifluoromethyl) benzonitrile,
4-(2,4-dioxo 1,3-diazaspiro(4.4)nonan-3-yl) 2-(trifluoromethyl) benzonitrile,
4-(2,4-dioxo 1-(2-fluoroethyl) 1,3-diazaspiro(4.4)nonan-3-yl) 2-(trifluoromethyl) benzonitrile,
1,5-dimethyl 5-(fluoromethyl) 3-(4-nitro 3-(trifluoromethyl) phenyl) 2,4-imidazolidinedione,
3-(4-cyano 3-(trifluoromethyl) phenyl) 2,4-dioxo 5-(fluoromethyl) 5-methyl 1-imidazolidinacetonitrile, 4-(4,4-bis-(fluoromethyl) 3-methyl 5-oxo 2-thioxo 1-imidazolidinyl 2-(trifluoromethyl) benzonitrile.

The products can be administered by parenteral, buccal, perlingual, rectal or topical route.

Also a subject of the invention is the pharmaceutical compositions, characterized in that they contain, as active ingredient, at least one of the medicaments of formulae (I), (Ia) and the cited products as defined above.

These compositions can be presented in the form of injectable solutions or suspensions, tablets, sugar-coated tablets, capsules, syrups, suppositories, creams, ointments and lotions. These pharmaceutical forms are prepared according to the usual methods. The active ingredient can be incorporated with excipients usually employed in these compositions, such as aqueous or non-aqueous vehicles, talc, gum arabic, lactose, starch, magnesium stearate, cocoa butter, fatty substances of animal or vegetable origin, paraffin derivatives, glycols, various wetting, dispersing or emulsifying agents, preservatives.

The usual dose, variable according to the patient being treated and the affection in question, can be, for example, from 10 mg to 500 mg per day for man, by oral route.

The products of formula (II) used at the start of the invention can be obtained by the action of phosgene when X represents an oxygen atom or thiophosgene when X represents a sulphur atom on the corresponding amine of formula (A):

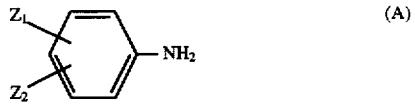

(A)

An example of such a preparation is given hereafter in the experimental part. A product of this type is also described in the French Patent BF 2,329,276.

The amines of formula (A) are described in the European Patent EP 0,002,892 or the French Patent BF 2,142,804.

The products of formula (III) or (III') are known or can be prepared from the corresponding cyanhydrin according to the process described in the publications: J. Am. Chem. Soc. (1953), 75, 4841, BEIL I 4 526 or J. Org. Chem. 27 2901 (1962).

The products of formula (III) in which R'$_3$ is different from a hydrogen atom can be obtained by the action of a product of formula R"$_3$ Hal on 2-cyano 2-amino propane under the conditions set out above for the action of R"$_3$ Hal on the products of formula (IV). An example of this type of preparation is described in the reference: Jilek et al. Collect. Czech. Chem. Comm. 54(8) 2248 (1989).

The products of formula (IV') are described in the French Patent BF 2,329,276.

The products of formulae (V) and (VI), used at the start of a process which is a subject of the invention, for obtaining the products of formulae (I), (I$_a$) as defined above, are known and commercially available or can be prepared according to methods known to a man skilled in the art.

The preparation of products of formula (VI) is described in particular in the following publications:

Zhur. Preklad. Khim. 28, 969–75 (1955) (CA 50, 4881a, 1956)

Tetrahedron 43, 1753 (1987)

J. Org. 52, 2407 (1987)

Zh. Org. Khim. 21, 2006 (1985)

J. Fluor. Chem. 17, 345 (1981) or in the Patents:

German Patent DRP 637,318 (1935)

European Patent EP 0,130,875

Japanese Patent JP 81,121,524.

The products of formula (VI) which are derivatives of hydantoin are widely used and mentioned in the literature such as for example in the following articles:

J. Pharm. Pharmacol., 67, Vol. 19(4), p. 209–16 (1967)

Khim. Farm. Zh., 67, Vol. 1(5) p. 51–2

German Patent 2,217,914

European Patent 0,091,596

J. Chem. Soc. Perkin. Trans. 1, p. 219–21 (1974).

Also a subject of the invention is, as new industrial products and notably as new industrial products which can be used as intermediates for the preparation of the products of formulae (I), (I$_a$) and the cited products as defined above, the products of formula (IVi):

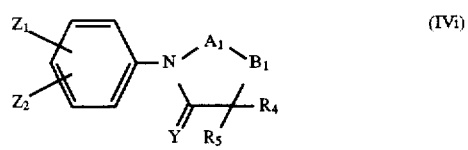

(IVi)

in which $Z_1$, $Z_2$, $R_4$, $R_5$ and Y have the meanings indicated above and the group:

is chosen from the radicals:

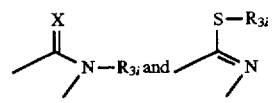

in which X represents an oxygen or sulphur atom and $R_{3i}$ is chosen from the values of $R_3$ containing a protected reactive function, with the exception of the products in which $R_4$ and $R_5$, identical or different, represent a hydrogen atom or an alkyl radical having 1 to 12 carbon atoms optionally substituted by one or more halogen atoms.

Among the reactive functions which can be protected the hydroxyl and amino functions can be mentioned. These functions can be protected as indicated above for the substituent $R_3$.

The following examples illustrate the invention without however limiting it.

EXAMPLE 1

2-(trifluoromethyl) 4-(4-(hydroxymethyl) 4-methyl 2,5-dioxo 1-imidazolidinyl) benzonitrile Stage A: 1-(tetrahydro 2H-pyran-2-yl) oxy) 2-propanone 50 g of hydroxyacetone, 100 cm³ of methylene chloride and 0.5 g of 1% monohydrated paratoluene sulphonic acid are introduced together. Then over 5 hours at 20° C., 62.44 g of 3,4-dihydro 2-pyran is added. After 2 hours 30 minutes of introduction, 0.5 g of paratoluene sulphonic acid is added then the mixture is agitated for one hour 30 minutes and 100 cm³ of water saturated with sodium bicarbonate is added. Agitation is carried out for 5 minutes at an alkaline pH then the reaction medium is decanted and extraction is carried out with methylene chloride, then the extracts are washed with water, the organic phases are dried, filtered and brought to dryness. 101.8 g of expected product is obtained (pale yellow oil).

Stage B: 2-amino 2-methyl 3-((tetrahydro 2H-pyran 2-yl) oxy) propanenitrile 77.3 g of potassium cyanide, 178.1 g of alumina and 70 g of ammonium chloride in 1 litre of acetonitrile are agitated under ultrasound for one hour while maintaining the temperature at 40° C.

Next 95 g of the product obtained in Stage A) above is added, then the mixture is rinsed with 0.2 l of acetonitrile and agitated for about 21 hours.

Filtration is carried out, followed by rinsing with acetonitrile and drying. Purification is carried out on silica (eluant: cyclohexane—ethyl acetate 1—1) and 65.5 g of expected product (yellow oil) is collected.

IR Spectrum: CHCl$_3$
C≡N 2230
NH 3393
3330

Stage C: 2-(trifluoromethyl) 4-(4-(hydroxymethyl) 4-methyl 2,5-dioxo 1-imidazolidinyl) benzonitrile a) Condensation 2-(trifluoromethyl) 4-[5-imino 4-methyl 2-oxo 4-[[(tetrahydro 2-H-pyran 2-yl) oxy] methyl] 1-imidazolidinyl] benzonitrile 12.77 g of the product obtained in Stage B above is introduced at 20° C.±2° C. into 127.7 ml of methylene chloride. Then over about 1 hour 30 minutes, under agitation at -30° C. ±3° C., a previously-filtered solution of 11.4 g of the product obtained in the preparation of Example 7 of the European Patent Application EP 0,494,819 in 171 ml of methylene chloride is added and agitation is carried out for about one hour at -30° C.±3° C. then the solvent is evaporated off under reduced pressure at 40° C. 24.7 g of the expected condensation product is obtained, used as it is for the methanolic hydrolysis.

b) Hydrolysis 2-(trifluoromethyl) 4-(4-(hydroxymethyl) 4-methyl 2,5-dioxo 1-imidazolidinyl) benzonitrile 21.3 g of the product obtained above in a is introduced under agitation at 20° C.±2° C., into 213 ml of methanol. Then 67 ml of 2N hydrochloric acid is added over 2 minutes. The mixture is taken to reflux for one hour then left to cool under agitation. After concentration by distilling off about 100 ml of methanol, the reaction medium is placed under magnetic stirring for about one hour at a temperature of 0°/+5° C. then separated.

The crystals obtained are purified, 3 volumes of methanol are added, followed by taking to reflux for 15 minutes, then leaving to cool down under agitation at 20°-25° C. and separating. 10.7 g of expected product (white crystals) is obtained. M.p.=218° C.

| Microanalysis: | | |
|---|---|---|
| | Theoretical | Product dried at 60° C. |
| C % | 49.85 | 49.7 |
| N % | 13.4 | 13.4 |
| F % | 18.19 | 18.0 |
| H % | 3.22 | 3.2 |

IR complex absorption OH/NH region
—C≡N approx. 2230 cm$^{-1}$
>=O 1780–1735 cm$^{-1}$
Aromatics 1604–1575–1503 cm$^{-1}$

EXAMPLE 2

2-(trifluoromethyl) 4-(4-(hydroxymethyl) 3, 4dimethyl 2,5-dioxo 1-imidazolidinyl) benzonitrile 1) Formation of tetrahydropyranic ether 626 mg of the product of Example 1, 10 ml of tetrahydrofuran, 30 mg of paratoluene sulphonic acid, H$_2$O and 2 ml of dihydropyran are introduced together. At end of about 30 minutes, the mixture is poured into 10 ml of sodium bicarbonate and 1 ml of triethylamine and extracted with chloroform. The organic phase is washed with salt water, dried and the solvent is evaporated off. Purification is carried out on silica (eluant: CH$_2$Cl$_2$, MeOH). 830 mg of the expected ether is obtained.

2) Methylation of the nitrogen 103 mg of 50% sodium hydride is introduced and 830 mg of the ether obtained above in 1) in 7 ml dimethylformamide is added over about 40 minutes, then 10 minutes after the cessation of the release of hydrogen, the reaction medium is placed in a water bath and 0.18 ml of methyl iodide and 0.5 ml of dimethylformamide are added. After reaction for 30 minutes, the medium is poured into 40 ml of water containing about 0.5 g of monopotassium phosphate and extracted with ether, then the organic phase is washed with salt water, dried and the solvent is evaporated off under reduced pressure. Purification is carried out on silica (eluant: CH$_2$Cl$_2$—Me$_2$CO (95-5)). 770 mg of product is obtained, used as it is for the following stage.

3) Hydrolysis of the tetrahydropyranic ether 770 mg of the N-methylated ether obtained above in 2) is introduced into 10 ml of methanol, 1.5 ml of 2N hydrochloric acid and heated at about 40° C.

After 30 minutes, the mixture is taken to ambient temperature, poured into 20 ml of sodium bicarbonate, extraction is carried out with chloroform, the extracts are washed with salt water, dried and the solvent is evaporated off under reduced pressure. Purification is carried out on silica (eluant: CH$_2$Cl$_2$—Me$_2$CO (3-1)). 111 mg of the crude product obtained above is recrystallized from 5 ml of hot isopropanol, concentrated to about 1 ml and ice-cooled for 16 hours. After filtration and drying, 90 mg of the expected product is, obtained (white crystals) M.p.=178°–179° C.

| Microanalysis | | | | |
|---|---|---|---|---|
| | C | H | F | N |
| % calculated | 51.38 | 3.70 | 17.41 | 12.84 |
| % found | 51.5 | 3.7 | 17.5 | 12.8 |

IR CHCl$_3$
OH 3620 cm$^{-1}$
>=O 1781–1728 cm$^{-1}$
C≡N 2235 cm$^{-1}$
Aromatics 1615–1576–1505 cm$^-$
UV EtOH
Max 262 nm ε=13900
Infl 278 nm ε=7200
Infl 286 nm ε=3800

EXAMPLE 3

4-(2,5-dioxo 3-(2-fluoroethyl) 4-(hydroxymethyl) 4-methyl 1-imidazolidinyl) 2-(trifluoromethyl) benzonitrile a) Alkylation with 1,2-bromofluoroethane 830 mg of the ether obtained in Stage 1) of Example 2 and 7.5 ml of dimethylsulphoxide are added drop by drop to 104 mg of 5% sodium hydride. About 20 minutes after cessation of the release of hydrogen, 0.22 ml of 1,2-bromofluoroethane is added in one lot. After about one hour of reaction, the medium is poured into 5 ml of water containing 500 mg of monopotassium phosphate and extracted with ether. The organic phase is washed with water then with salt water, dried and the solvent is evaporated off under reduced pressure. Purification is carried out on silica (eluant: $CH_2Cl_2$—$Me_2CO$ (97.5–2.5)) and 743 mg of expected 25 product is obtained.

b) Hydrolysis of the tetrahydropyranic ether 743 mg of the product obtained above in 1) is introduced into 10 ml of methanol, 1.5 ml of 2N hydrochloric acid and the mixture is taken to 40° C. then after 45 minutes is poured into 20 ml of sodium bicarbonate and extracted with chloroform. The organic phase is washed with salt water, dried and the solvent is evaporated off under reduced pressure. Purification is carried out on silica (eluant: $CH_2Cl_2$—$Me_2CO$ (9–1)) then the crystals obtained are dissolved in 20 ml of isopropanol at 60° C., followed by filtration, rinsing and concentrating to about 5 ml, ice-cooling for about one hour and separating. 466 mg of the expected product (white crystals) is obtained. M.p.=146°–147° C.

Microanalysis

|  | C | H | F | N |
|---|---|---|---|---|
| % calculated | 50.15 | 3.65 | 21.15 | 11.70 |
| % found | 50.1 | 3.50 | 20.9 | 11.7 |

IR $CHCl_3$
OH 3612 $cm^{-1}$
>=O 1782 (m)–1727 (f) $cm^{-1}$
C≡N 2235 $cm^{-1}$
UV EtOH
Max 260 nm ε=15500
Infl 278 nm ε=6700
Infl 286 nm ε=3300

EXAMPLE 4

4-(3,4-dimethyl) 4-(hydroxymethyl) 5-oxo 2-thioxo 1-imidazoliLdinyl) 2-(trifluoromethyl) benzonitrile Staqe A:(±) 2-methyl 2-(methylamino) 3-[(tetrahydro 2-H pyran 2-yl) oxy] propanenitrile 1.54 g of methylamine hydrochloride in solution in 10 $cm^3$ of water and 3.35 g of the ketone obtained in Stage A of Example 1 are introduced together and the suspension obtained is agitated for about 10 minutes.

1.06 g of NaCN in solution in 5 $cm^3$ of water is poured into the mixture and agitation is carried out overnight at ambient temperature.

Extraction is carried out with methylene chloride, the extracts are washed with a saturated solution of sodium chloride, dried and the solvent is evaporated off under reduced pressure. 3.72 g of expected product (yellow oil) is obtained, used as it is for the following stage.
IR $CHCl_3$
NH approx. 3345 $cm^{-1}$
C≡N approx. 2230 $cm^{-1}$.

Staqe B: 2-(trifluoromethyl) 4-[5-imino 3,4-dimethyl 4-[[(tetrahydro 2-H-pyran 2-yl) oxy] methyl] 2-thioxo 1-imidazolidinyl] benzonitrile 2.38 q of aminonitrile in solution in 8 $cm^3$ of 1,2-dichloroethane is introduced and 0.5 $cm^3$ of triethylamine is added, the mixture is cooled down to a temperature of –5° to 0° C. and 2.75 g of the isothiocyanate obtained in the preparation of Example 11 of the European Patent Application EP 0,494,819 in solution in 17 $cm^3$ of 1,2-dichloroethane is poured in over 20 minutes at a temperature below 0° C. The reaction medium is left to return to ambient temperature and agitation is maintained for about 2 hours, followed by drying and evaporating the solvent under reduced pressure.

After purification on silica (eluant: $CH_2Cl_2$—acetone (92–8)), 3.31 g of expected product is obtained.
IR $CHCl_3$
>C=NH 3308 $cm^{-1}$
—C≡N 2236 $cm^{-1}$
>C=N 1679 $cm^{-1}$
>C=S 1614 $cm^{-1}$
Aromatic 1575 $cm^{-1}$
1505 $cm^{-1}$
1496 $cm^{-1}$ Stage C: 4-(3,4-dimethyl) 4-(hydroxymethyl) 5-oxo 2-thioxo 1-imidazolidinyl) 2-(trifluoromethyl) benzonitrile 19 $cm^3$ of 2N hydrochloric acid is added drop by drop to 3.25 g of the product obtained in Stage B above, in solution in 35 $cm^3$ of methanol, and the whole is taken to reflux for 35 minutes.

Neutralization is carried out with a solution of sodium bicarbonate, followed by extraction with chloroform, the organic phase is washed with a saturated solution of sodium chloride, dried and the solvent is evaporated off under pressure. After purification on silica (eluant: $CH_2Cl_2$—ACOEt (85–15), then recrystallization from 10 $cm^3$ of isopropanol, 1.90 g of expected product (white crystals) is obtained. M.p.=167°–168° C.

Microanalysis

|  | C | H | N | F | S |
|---|---|---|---|---|---|
| % calculated | 48.98 | 3.52 | 12.24 | 16.60 | 9.34 |
| % found | 48.9 | 3.6 | 12.1 | 16.7 | 9.1 |

IR $CHCl_3$
Absence of C=NH
—OH 3620 $cm^{-1}$
>C=O 1759 $cm^{-1}$
>C≡N 2238 $cm^{-1}$
Aromatics 1610 $cm^{-1}$
+1576 $cm^{-1}$
conjugated 1505 $cm^{-1}$
system 1494 $cm^{-1}$

EXAMPLE 5

1,5-dimethyl 5-(hydroxymethyl) 3-(4-nitro 3-(trifluoronmethyl) phenyl) 2,4-imidazolidinedione Stage A: Formation of tetrahydropyranic ether The operation is carried out as in 1) of Example 2 above, replacing in this preparation the product of Example 1 by 870 mg of the product obtained as in Example 2 of the European Patent Application EP 0,305,270 in 13 ml of tetrahydrofuran, 40 mg of paratoluene sulphonic acid, $H_2O$, 2.6 ml of dihydropyran. After about 15 minutes, the reaction mixture is poured into 10 ml of a saturated solution of sodium bicarbonate and 1 ml of triethylamine and extracted with chloroform. The organic phase is washed with salt water, dried, the solvent is evaporated off under reduced pressure and purification is carried out on silica (eluant: $CH_2Cl_2$—MeOH (95–5)) and the expected product is obtained.

Stage B: Methylation of the nitrogen

The operation is carried out as in 2) of Example 2 above, starting from the product obtained in 1) above, and the expected product is obtained.

Stage C: Hydrolysis of the tetrahydropyranic ether.

The operation is carried out as in 3) of Example 2 above, starting from 955 mg of the product obtained in 2) above and 698 mg of expected product (white crystals) is obtained. M.p.=153°–154° C.

Microanalysis

|  | C | H | F | N |
|---|---|---|---|---|
| % calculated | 44.96 | 3.48 | 16.41 | 12.10 |
| % found | 45.0 | 3.50 | 16.3 | 12.1 |

IR $CHCl_3$
OH 3620 $cm^{-1}$
>C=O 1782–1727 $cm^{-1}$
Aromatic 1618–1596–1545–1498 $cm^{-1}$
and $NO_2$ band
UV EtOH
Infl 214 nm ε=13000
Max 271 nm ε=6100
Infl 320 nm

EXAMPLE 6

4-(4-(fluoromethyl) 3,4-dimethyl) 2,5-dioxo 1-imidazolidinyl) 2-(trifluoromethyl) benzonitrile 0.2 ml of diethylaminosulphide trifluoride, then drop by drop the solution cooled down to –60° C. of 0.2 g of the product of Example 2 and 6.5 ml of tetrahydrofuran, are added to 1 ml of tetrahydrofuran, cooled down to about –60° C.

The resultant mixture is left to return to ambient temperature, then heated at 30° C. After one hour, the reaction medium is poured into 18 ml of sodium bicarbonate and extracted with ether. The organic phase is washed with salt water, dried and the solvents are evaporated off under reduced pressure. Purification is carried out on silica (eluant: $CH_2Cl_2$—cyclohexane (9–1)) then the crystals obtained are dissolved in 30 ml of isopropanol at 60° C., followed by filtration, rinsing with 2 ml of isopropanol, concentration to about 5 ml and ice-cooling overnight. After separation and drying, 136 mg of expected product (white crystals) is obtained. M.p.=153°–154° C.

Microanalysis

|  | C | H | F | N |
|---|---|---|---|---|
| % calculated | 51.07 | 3.37 | 23.08 | 12.76 |
| % found | 50.8 | 3.2 | 25.0 | 12.7 |

IR $CHCl_3$
C≡N 2240 $cm^{-1}$
>C=O 1785–1733 $cm^{-1}$
Aromatic 1616–1575–1505 $cm^{-1}$
UV EtOH
Max 259 nm ε=15200
Infl 278 nm ε=5800
Infl 286 nm ε=2900

EXAMPLE 7

4-(3,4-dimethyl) 4-(fluoromethyl) 5-oxo 2-thioxo 1-imidazolidinyl) 2-(trifluoromethyl) benzonitrile 2 $cm^3$ of anhydrous tetrahydrofuran is cooled down to –60° C. and drop by drop over about 15 minutes at a temperature comprised between –60° C. and –53° C., 0.88 $cm^3$ of diethylamino-sulphide trifluoride then 0.930 g of the product of Example 4 in solution in 7 $cm^3$ of anhydrous tetrahydrofuran are poured in drop by drop. After the reaction medium has returned to ambient temperature, it is maintained for about 30 minutes at about 30° C. It is then poured into 25 $cm^3$ of a solution of sodium bicarbonate and ice. Extraction is carried out with ether, the ethereal phase is washed with a saturated solution of sodium chloride, dried and the solvents are evaporated off under reduced pressure. After purification on silica (eluant: $CH_2Cl_2$—cyclohexane (9–1)) and recrystallization from isopropanol, 1.010 g of expected product (white crystals) is obtained after drying. M.p.=163° C.

Microanalysis

|  | C | H | F | N | S |
|---|---|---|---|---|---|
| % calculated | 48.69 | 3.21 | 22.01 | 12.17 | 9.28 |
| % found | 48.6 | 3.10 | 22.2 | 12.1 | 9.5 |

IR $CHCl_3$
Absence of OH
N≡C approx. 2238 $cm^{-1}$
>C=O 1762 $cm^{-1}$
Conjugated syst.+1615–1580 $cm^{-1}$
Aromatic 1505–1491 $cm^{-1}$
UV EtOH
Max 235 nm ε=19200
Max 253 nm ε=23000
Infl 265 nm ε=18300

EXAMPLE 8

4-(2,5-dioxo 3-(2-fluoroethyl) 4-(fluoromethyl) 4-methyl 1-imidazolidinyl) 2-(trifluoromethyl) benzonitrile 1 ml of tetrahydrofuran is cooled down to –50° C. and 0.33 ml of diethylaminosulphide trifluoride is added then a solution cooled down beforehand to about –50° C. of 360 mg of the product of Example 3 and 4 ml of tetrahydrofuran is added drop by drop. Rinsing is carried out with 0.5 ml of tetrahydrofuran and the medium is left to return to ambient temperature then taken to about 30° C. It is then poured into 30 ml of sodium bicarbonate and 10 g of ice and extracted with chloroform then the organic phase is washed with salt water and dried. Purification is carried out on silica (eluant: $CH_2Cl_2$—ethyl acetate (99–1)) then the crystals obtained are dissolved in 30 ml of isopropanol under reflux, followed by filtration, rinsing with 1 ml of isopropanol, concentration to about 7 ml and leaving at rest for 16 hours at 0° C. After separation and drying, 307 mg of expected product (white crystals) is obtained. M.p.=137°–138° C.

Microanalysis

|  | C | H | F | N |
|---|---|---|---|---|
| % calculated | 49.87 | 3.35 | 26.29 | 11.63 |
| % found | 49.8 | 3.4 | 26.2 | 11.6 |

IR $CHCl_3$
C≡N 2235 $cm^{-1}$
>=O 1786–1730 $cm^{-1}$
Aromatic 1616–1575–1505 $cm^{-1}$
UV EtOH Max 258 nm ε=16000
Infl 277 nm ε=5300
Infl 285 nm ε=2700

EXAMPLE 9

4-(2,4-dioxo 1,3-diazaspiro(4,4)nonan 3-yl) 2-(trifluoronmethyl) benzonitrile Stage A: 1-amino cyclopentanecarbonitrile 40 ml of ammonium hydroxide, 7.9 g of ammonium chloride and 6.14 g of sodium cyanide are introduced together then agitation is carried out until total dissolution in an ice bath at a temperature of −8° C. Then 8.8 ml of cyclopentanone is added drop by drop at a temperature of about −9° C., the reaction medium is left to return to ambient temperature and agitated overnight.

The organic phase is then decanted, the aqueous phase is extracted with methylene chloride, then the organic phases are washed with salt water and dried. After distillation at 55° C.±2° C., 1.2 g of expected product is obtained.

IR CHCl$_3$
NH$_2$ 3381–3330 cm$^{-1}$
C≡N 2226 cm$^{-1}$
Absence C=O

Stage B: 2-(trifluoromethyl) 4-[4-imino 2-oxo 1,3-diazaspiro[4.4]nonan 3-yl] benzonitrile 550 mL of the product obtained in Stage A above, 4 ml of 1,2-dichlo:coethane and 0.2 ml of triethylamine are introduced together then the mixture is brought to 0° C. and 3.1 ml of the product obtained in the preparation of Example 7 of the European Patent Application EP 0,494,819 is added over 5 minutes at a temperature of −4° C. and the whole is left to return to ambient temperature.

After about 40 minutes of reaction the medium is concentrated to dryness, the residue is dissolved in 40 ml of acetone, the solvent is evaporated off and purification is carried out on silica (eluant: CH$_2$Cl$_2$—Me$_2$CO (90–10)). 1.24 g of expected product (white crystals) is obtained. M.p.=212°–213° C.

IR nujol
OH/NH 3350–3280 cm$^{-1}$
CH≡2240 cm$^{-1}$
C=O 1744 cm$^{-1}$
>=N 1670 cm$^{-1}$
Aromatic 1610–1574–1510 cm$^{-1}$ Stage C: 4-(2,4-dioxo 1,3-diazaspiro(4,4)nonan 3-yl) 2-(trifluoromethyl) benzonitrile 1.17 g of the product obtained in Stage B above in 20 ml of methanol, 3 ml of chloroform and 5 ml of 2N hydrochloric acid are introduced together then taken to about 50° C. for about 2 hours.

The mixture is taken to ambient temperature, poured into 40 ml of water and extracted 3 times with methylene chloride. The organic phase is washed with salt water, dried and the solvent is evaporated off under reduced pressure, then purification is carried out on silica (eluant: CH$_2$Cl$_2$—Me$_2$CO (9–1)). 1.108 g of expected product (white crystals) is obtained. M.p.=184°–185° C.

| | Microanalysis | | | |
|---|---|---|---|---|
| | C | H | F | N |
| % calculated | 55.73 | 3.74 | 17.63 | 13.00 |
| % found | 55.6 | 3.7 | 17.4 | 12.8 |

IR CHCl$_3$
=C—NH 3444 cm$^{-1}$
C≡N 2236 cm$^{-1}$
>=O 1786–1731 cm$^{-1}$
Aromatic 1616–1505 cm$^{-1}$
UV EtOH
Max 258 nm ε=15600
Infl 286 nm ε=3500

EXAMPLE 10

4-(2,4-dioxo 1-(2-fluoroethyl) 1,3-diaza-spiro(4.4) nonan-3-yl) 2-(trifluoromethyl) benzonitrile 0.323 g of the product of Example 9 in solution in 2.5 cm$^3$ of dimethylsulphoxide is poured drop by drop over about 20 minutes into 0.050 g of sodium hydride at 50% in oil. Agitation is carried out for about one hour 20 minutes then 0.09 cm$^3$ of 1-bromo 2-fluoroethane in solution in 0.2 cm$^3$ of dimethylsulphoxide is poured in drop by drop. After about 2 hours at ambient temperature, the reaction medium is heated for 10 minutes at between 30° and 35° C., then poured into 12 cm$^3$ of water containing 0.2 g of monosodium phosphate and extracted with ether. The ethereal phase is washed with a saturated solution of sodium chloride, dried and evaporated to dryness. Purification is carried out on silica (eluant: CH$_2$Cl$_2$—ethyl acetate (99–1)) and 0.249 g of expected product is obtained. M.p.=115° C.

| | Microanalysis | | | |
|---|---|---|---|---|
| | C | H | F | N |
| % calculated | 55.29 | 4.09 | 20.58 | 11.38 |
| % found | 55.3 | 4.1 | 20.25 | 11.3 |

IR CHCl$_3$
—C≡N 2238 cm$^{-1}$
—C=O 1776–1723 cm$^{-1}$
Aromatic 1616–1575–1505 cm$^{-1}$
UV EtOH
Max 260 nm ε=15600
Infl 287 nm

EXAMPLE 11

1,5-dimethyl 5-(fluoromethyl) 3-(4-nitro 3-(trifluoromethyl) phenyl) 2,4-imidazolidinedione 0.09 ml of diethylaminosulphide trifluoride is added to 1 ml of tetrahydrofuran, cooled down to about −60° C., and drop by drop a solution cooled down to about −60° C. of 210 mg of the product of Example 5 and 2.5 ml of tetrahydrofuran is added. The mixture is rinsed with 0.5 ml of tetrahydrofuran, left to return to ambient temperature, taken to a temperature of about −65° C. and 0.1 ml of diethylaminosulphide trifluoride is added.

After one hour 20 minutes, the reaction medium is poured into 8 ml of sodium bicarbonate and extracted with ether. The organic phase is washed with salt water, dried, the solvent is evaporated off under reduced pressure and purification is carried out on silica with CH$_2$Cl$_2$—Me$_2$CO (99–1) as eluant. 152 mg of expected product (white crystals) is obtained. M.p.=118°–119° C.

| | Microanalysis | | | |
|---|---|---|---|---|
| | C | H | F | N |
| % calculated | 44.71 | 3.17 | 21.76 | 12.03 |
| % found | 44.9 | 3.1 | 21.42 | 11.9 |

IR CHCl$_3$
—C=O 1786–1732 cm$^{-1}$
Aromatic and 1618–1597–1546–1498 cm$^-$
UV EtOH
Infl 214 nm ε=13400
Max 267 nm ε=6200
Infl 320 nm

EXAMPLE 12

4-(4,4-dimethyl-2,5-dioxo-3-(2-(2-hydroxyethoxy) ethyl)-1-iniidazolidinyl-2-(trifluoromethyl)-benzonitrile Stage 1: 4-(4,4-dimethyl-2,5-dioxo-3-(2-(2-(((1,1-dimethyl-ethyl) dimethylsilyl) oxy) ethoxy) ethyl)-1-imidazolidinyl-2(trifluoromethyl)-benzonitrile The solution of 0.594 g of the product of Example 8 of EP 0,494,819 and 4.5 ml of dimethylsulphoxide are poured drop by drop over 15 minutes into 0.101 g of sodium hydride at 50% in oil and agitation is carried out for 30 minutes after cessation of the release of hydrogen.

0.594 g of (2-(2-bromoethoxy) ethoxy)-dimethyl-(1,1-dimethylethyl) silane in solution in 1 ml of dimethylsulphoxide is poured in drop by drop over 5 minutes.

Agitation is carried out for one hour at ambient temperature then 0.056 g of (2-(2-bromoethoxy) ethoxy)-dimethyl-(1,1-dimethyl-ethyl) silane is added and the whole is maintained for 2 hours 30 minutes between 30° C. and 40° C.

The mixture is poured into 0.6 g of monosodium phosphate and 30 ml of ice-cooled water and extracted with ether.

The ethereal phase is washed with a solution of NaCl, dried and the solvent is evaporated off.

After chromatography on silica (eluant: methylene chloride/ethyl acetate 99/1), 0.776 g of expected product (oil) is isolated.
IR CHCl$_3$ cm$^{-1}$
Absence of =C—NH
—CN approx. 2235

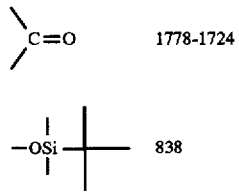

Aromatic 1616–1577–1505
Stage 2: 4-(4,4-dimethyl-2,5-dioxo-3-(2-(2-hydroxyethoxy) ethyl)-1-imidazolidinyl)-2-(trifluoromethyl)-benzonitrile 0.759 g of the product obtained in Stage 1 above is introduced into 7.5 ml of methanol and 2 ml of 2N hydrochloric acid is added drop by drop.

The mixture is agitated for 40 minutes at ambient temperature, poured into ice-cooled water and extracted with chloroform.

The organic phase is washed with a saturated solution of sodium chloride and dried; the solvent is evaporated off then chromatography is carried out on silica (eluant: methylene chloride/acetone 9/1), and 0.549 g of expected product is isolated. M.p.<60° C.

ANALYSES

IR CHCl$_3$ (cm$^{-1}$)
Complex —OH towards 3610–3620
—CN approx. 2235
C=O 1779–1725
Aromatics 1616–1575–1505

EXAMPLE 13

4-(4,4-dimethyl 2,5-dioxo 3-(2-fluoroethyl) 1-imidazolidinyl) 2-(trifluoromethyl) benzonitrile The solution of 600 mg of the product of Example 8 of the European Patent Application EP 0,494,819 and 5 ml of dimethylformamide is added drop by drop over about 20 minutes to 104 ml of 50% sodium hydride. The mixture is rinsed with 0.5 ml of dimethylformamide and after cessation of the release of hydrogen, 0.16 ml of 1-bromo 2-fluoroethane is added. A further 98 ml of 50% sodium hydride is then added and after approximately 10 minutes, 0.1 ml of 1-bromo 2-fluoroetharie is added and the whole is heated to 50° C. It is returned to ambient temperature, poured into 20 ml of water containing 200 mg of monopotassium phosphate and extracted with ether The extracts are washed with water then with salt water, dried, the solvent is evaporated off under reduced pressure, followed by dissolution in 20 ml of Me$_2$CO and purification on silica (eluant CH$_2$Cl$_2$ —ethyl acetate (99–1)). 200 mg of expected product (white crystals) is obtained. M.p.=10° C.8–109° C.

| | Microanalysis | | | |
|---|---|---|---|---|
| | C | H | F | N |
| % calculated | 52.48 | 3.82 | 22.14 | 12.24 |
| % found | 52.4 | 3.7 | 22.00 | 12.4 |

IR CHCl$_3$
C≡N 2236 cm$^{-1}$
C=O 1780–1728 cm$^{-1}$
Aromatic 1618–1580–1504 cm$^{-1}$

EXAMPLE 14

4-(4,4-dimethyl 2,5-dioxo 3-(2,2,2-trifluoro-ethyl) 1-irnidazolidinyl) 2-(trifluoromethyl) benzonitrile 0.742 g of the product of Example 8 of the European Patent Application EP 0,494,819 in solution in 7.5 cm$^3$ of dimethylsulphoxide is poured over 20 minutes into 0.125 g of sodium hydride at 50% in oil and the resultant mixture is rinsed with 1 cm$^3$ of dimethylsulphoxide. After the release of hydrogen is complete, agitation is maintained for about 20 minutes and 0.5 cm$^3$ of iodotrifluoromethane is poured in and 0.5 cm$^3$ of 15-crown-5 ether is added. The mixture is maintained at 60° C. for 16 hours. After addition of 0.25 cm$^3$ of iodotriifluoromethane, heating is continued for about 19 hours at 80° C. The reaction medium is then poured into 30 cm$^3$ of water +0.5 g of monosodium phosphate and extracted with ether The ethereal phase is washed with a saturated solution of sodium chloride, dried and evaporated to dryness. Purification is carried out on silica (eluant: CH$_2$Cl$_2$—ethyl acetate (99–1)), followed by recrystallization from 10 cm$^3$ of isopropanol and 0.262 g of expected product (white crystals) is obtained. M.p.=110° C.

| Microanalysis | | | | |
|---|---|---|---|---|
| | C | H | F | N |
| % calculated | 47.5 | 2.92 | 30.05 | 11.08 |
| % found | 47.3 | 2.8 | 30.0 | 11.0 |

IR CHCl$_3$
Absence of N—H
>C=O 1790–1732 cm$^{-1}$
Aromatic 1616–1578–1505 cm$^{-1}$
C≡N 2235 cm$^{-1}$
UV EtOH
Max 255 nm ε=16400
Infl 276 nm ε=4400
Infl 285 nm ε=2400

EXAMPLE 15

4-(4,4-dimethyl 3-(2-fluoroethyl) 5-oxo 2-thioxo 1-imidazolidinyl) 2-(trifluoromethyl) benzonitrile Stage A: 4-[3-(2-fluoroethyl) 5-imino 4,4-dimethyl 2-thioxo 1-imidazolidinyl] 2-(trifluoromethyl) benzonitrile 1.86 ci of 2-[(2-fluoroethyl) amino] 2-methyl propanenitrile and 0.55 cm$^3$ of triethylamine are introduced into 12 cm$^3$ of 1,2-dichloroethane. The mixture is cooled down to 0° C. and 2.97 g of the isothiocyanate obtained as in the preparation of Example 11 of the European Patent Application EP 0.494.819 in solution in 22 cm$^3$ of 1,2-dichloroethane is poured in over about 25 minutes at a temperature of about 0° C. Agitaition is continued for 7 hours at ambient temperature then the solvent is evaporated off under reduced pressure. Purification is carried out on silica (eluant: CH$_2$Cl$_2$—acetone (95–5) then (97–3)), the residue is taken up in a few cm$^3$ of ether, followed by separating, drying, and 1.84 g of expected product is obtained. M.p.=160° C.
IR CHCl$_3$
C=NH 3308 cm$^{-1}$
C≡N 2236 cm$^{-1}$
Conjugated system 1677 cm$^{-1}$
+1604 cm$^{-1}$
aromatics 1576–1504 cm$^{-1}$ Stage B: 4-(4,4-dimethyl 3-(2-fluoroethyl) 5-oxo 2-thioxo 1-imidazolidinyl) 2-(trifluoromethyl) benzonitrile 6.9 cm$^3$ of 2N hydrochloric acid is added drop by drop to 1.65 g of the product obtained in Stage A above, in solution in 60 cm$^3$ of methanol. After about one hour 30 minutes at 50° C., the mixture is neutralized with sodium bicarbonate and the methanol is distilled off. The residue is taken up in water, followed by extraction with ether, the ethereal phase is washed with a solution of sodium chloride and dried. After purification on silica with CH$_2$Cl$_2$ as eluant and recrystallization from 15 cm$^3$ of isopropanol, 2.99 g of expected product (white crystals) is obtained. M.p.=135° C.

| Microanalysis | | | | | |
|---|---|---|---|---|---|
| | C | H | F | N | S |
| % calculated | 50.14 | 3.65 | 21.15 | 11.69 | 8.92 |
| % found | 50.1 | 3.60 | 21.0 | 11.7 | 9.2 |

IR CHCl$_3$
Absence of =C—NH
>C=O 1758 cm$^{-1}$
N≡C 2236 cm$^{-1}$
Conjugated syst. 1610 cm$^{-1}$
+1576 cm$^{-1}$
Aromatic 1504 cm$^{-1}$
UV EtOH
Max 233 nm ε=17700
Max 253 nm ε=21600

EXAMPLE 16

3-(4-cyano 3-(trifluoromethyl) phenyl) 2,4-dioxo 5-(hydroxymethyl) 5-methyl 1-imidazolidinacetonitrile The operation is carried out as in Example 2, starting with the product of Example 1, replacing the iodomethyl in 2) of Example 2 with bromocyanomethyl and in this way the expected product is obtained. M.p.=171° C.

EXAMPLE 17

3-(4-cyano 3-(trifluoromethyl) phenyl) 2,4-dioxo 5-(fluoromethyl) 5-methyl 1-imidazolidinacetonitrile The operation is carried out as for the preparation of Example 6, replacing the product of Example 2 with the product of Example 16 and in this way the expected product is obtained. M.p.=175° C.

EXAMPLE 18

(±) 4-[2-oxo 5-imino [[(4-fluorophenyl) thio] methyl] 4-methyl 1-imidazolidinyl 2-trifluoromethyl benzonitrile Stage A: (±) 3-[(4-fluorophenyl) thio] 2-amino 2-methyl propane nitrile A solution of 4.81 g of ammonium chloride in 12 ml of water and 24.6 ml of 25° C. Be ammonium hydroxide then a solution of 8.32 g of 1-[4-fluorophenylthio] 2-propanone prepared as indicated in the Patent 82 46399 E, in 21 ml of ethanol at 96.2%, are added successively to 2.21 g of sodium cyanide in 45 ml of water. The resultant mixture is maintained at 60° C. and agitated for about 22 hours. It is cooled down to 0° C./+4° C., rinsed with ethanol, distilled, decanted, the aqueous phase is extracted with CH$_2$Cl$_2$, washed with a saturated solution of sodium chloride, dried and the solvent is evaporated off under reduced pressure. Purification is carried out by chromatography on silica with cyclohexane—ethyl acetate (50—50) as eluant and 14.50 g of expected product is obtained.
IR CHCl$_3$
Absorption NM 3382–3327cm$^{-1}$
Aromatic 1591–1491 cm$^{-1}$
—C≡N 2228 cm$^{-1}$ Stage B: (±) 4-[2-oxo 5-imino [[(4-fluorophenyl) thio] methyl] 4-methyl 1-imidazolidinyl 2-trilfluoromethyl benzonitrile 9.8 g of the product obtained in Stage A above and 35 ml of 1,2-dichloroethane are mixed together, and 0.2 ml of triethylamine is added. The mixture is cooled down to 5° C. and the solution of 7.7 g of the product obtained in the preparation of Example 7 of the European Patent Application EP 0.494.819 and 40 ml of 1,2-dichloroethane is introduced over 12 minutes at a temperature between 5° C. and 10° C.

The reaction medium is rinsed with 5 ml of dichloroethane and left for 16 hours at ambient temperature. The solvent is evaporated off under reduced pressure, the residue is purified on silica (eluant: CH$_2$Cl$_2$—Me$_2$CO (93–7)), then dissolved in 100 ml of isopropanol at about 60° C., followed by filtration, rinsing with 20 ml of hot isopropanol, concentration, ice-cooling for about 3 hours, separation, rinsing with ice-cooled isopropanol and drying. 2.815 g of expected product (white crystals) is obtained, M.p.=150° C.

| | Microanalysis | | | | |
|---|---|---|---|---|---|
| | C | H | F | N | S |
| % calculated | 54.03 | 3.34 | 17.99 | 13.26 | 7.59 |
| % found | 54.1 | 3.30 | 17.9 | 13.1 | 7.7 |

IR $CHCl_3$
C=O 1756 $cm^{-1}$
C=N 1669 $cm^{-1}$
NH 3444 $cm^{-1}$
Aromatic 1614–1591–1505–1491 $cm^{-1}$
C≡N exists

EXAMPLE 19

4-[2,5-dioxo 4-[[(4-fluorophenyl) thio] methyl] 4-methyl 1-imidazolidinyl] 2-trifluoromethyl benzonitrile 3.95 q of the product obtained in Example 18, 14 ml of 22° C. Be hydrochloric acid and 14 ml of water are introduced together and the suspension is heated under reflux.

After about one hour 30 minutes, the suspension is returned to ambient temperature, poured over ice+water 100 g (1—1) and extracted with ethyl acetate. The organic phase is washed with water, then with a saturated solution of sodium bicarbonate, and finally with a saturated solution of sodium chloride and the solvent is evaporated off. Purification is carried out by chromatography on silica (eluant: $CH_2Cl_2$—$Me_2CO$ (95–5)). The residue is taken up in 50 ml of ethanol 100 at 50° C., followed by filtration, rinsing with 5 ml of hot ethanol, concentration and leaving for 16 hours in a refrigerator at about 0° C. to +4° C.

After separation, the product is rinsed with ice-cooled ethanol and dried. 3.55 g of expected product (white crystals) is obtained. M.p.=153° C.

| | Microanalysis | | | | |
|---|---|---|---|---|---|
| | C | H | F | N | S |
| % calculated | 53.9 | 3.09 | 17.95 | 9.92 | 7.57 |
| % found | 53.9 | 3.1 | 18.3 | 9.8 | 7.8 |

IR $CHCl_3$
C=O 1791–1734 $cm^{-1}$
NH 3439 $cm^{-1}$
C=N 2236 $cm^{-1}$
Aromatics 1615–1591–1505–1492 $cm^{-1}$

EXAMPLE 20

4-(2,5-dioxo 3-(2-fluoroethyl) 4-((4-fluoro-phenyl) thiomethyl) 4-methyl 1-imidazolidinyl 2-(trifluoromethyl) benzonitrile The solution of 0.254 g of the product obtained as in Example 19 in 2.2 $cm^3$ of dimethylsulphoxide is poured drop by drop over about 10 minutes onto 0.031 g of sodium hydride at 50% in oil. Agitation is maintained for about 40 minutes. Then the solution of 0.54 $cm^3$ of 1-bromo 2-fluoroethane in 0.7 $cm^3$ of dimethyl-sulphoxide is added drop by drop over about 5 minutes.

After agitation for 30 minutes, the reaction medium is poured onto 0.4 g of monosodium phosphate, water+ice. Extraction is carried out with ether, the organic phase is washed with a saturated solution of sodium chloride, dried and the solvent is evaporated off under reduced pressure. After purification on silica (eluant: $CH_2Cl_2$—ethyl acetate (100–0.5)) then recrystallization from 15 $cm^3$ of isopropanol. 0.175 g of expected product (white crystals) is obtained. M.p.=155° C.

| | Microanalysis | | | | |
|---|---|---|---|---|---|
| | C | H | F | N | S |
| % calculated | 53.73 | 3.43 | 20.23 | 8.95 | 6.83 |
| % found | 53.5 | 3.2 | 20.5 | 9.0 | 7.1 |

IR $CHCl_3$
Absence of =C—NH
C≡N approx. 2235 $cm^{-1}$
>C=O 1780–1727 $cm^{-1}$
Aromatics 1616–1591–1505–1492 $cm^{-1}$
UV EtOH
Max 255 nm $\epsilon$=18600
Infl 278 nm $\epsilon$=8000
Infl 287 nm $\epsilon$=4400

EXAMPLE 21

4-(4,4-bis(hydroxymethyl) 3-methyl 5-oxo 2-thioxo 1-imidazolidinyl) 2-(trifluoromethyl) benzonitrile Stage A: 2-(methylamino) 2-[[(tetrahydro 2-H-pyranl 2-yl) oxy] methyl] 3-(tetrahydro 2H-pyran 2-yl) oxy propanenitrile 2.7 g of 1,3-bis[(tetrahydro 2H-pyran-2-yl) oxy] 2propanone obtained as below, 5 ml of water and 0.77 g of methylamine hydrochloride are introduced together then 503 mg of sodium cyanide and 3 ml of water are added over 5 minutes. After 2 hours 30 minutes of reaction, extraction is carried out with methylene chloride, the organic phase is washed with salt water, the solvent is evaporated off under reduced pressure. 3.3 g of expected product is obtained, used as it is for the following stage.

IR $CHCl_3$
NH 3346 $cm^{-1}$
C≡N 2230 $cm^{-1}$
C=O 1732 $cm^{-1}$

Preparation of 1,3-bis-[(tetrahydro 2H-pyran 2-yl) oxy] 2-propanone used at the start of Example 21

9 g of 1,3-dihydroxyacetone dimer in suspension in 60 ml of dioxane is heated to 70° C. and returned to ambient temperature. 20 ml of 3,4-dihydro 2,4-pyran then 300 mg of paratoluene sulphonic acid and $H_2O$ are added, while maintaining the temperature below 40° C. The reaction medium is maintained for 16 hours under agitation, poured into 300 ml of a saturated solution of sodium bicarbonate, the organic phase is washed with salt water, dried and the solvent is evaporated off under reduced pressure. After chromatographing the residue on silica (eluant: cyclohexane—ethyl acetate—triethylamine (8—2—0.5)), 17 g of expected product is obtained. RF=0.2.

Stage B: 2-(trifluoromethyl) 4-[4,4-bis-[[(tetrahydro 2-H-pyran 2-yl) oxy] methyl] 5-imino 3-methyl 2-thioxo 1-imidazolidinyl] benzonitrile 2.39 cl of the isothiocyanate obtained in the preparation of Example 11 of the European Patent Application EP 0.494, 819 and 10 ml of 1,2-dichloroethane are mixed together. Then 3.2 g of the product obtained in Stage A above, 0.4 ml of triethylamine and 10 ml of 1,2-dichloroethane are added drop by drop to the solution cooled down to +5° C. After heating for about one hour 20 minutes, the solvent is evaporated off and purification is carried out on silica (eluant: ethyl acetate 7 c,yclohexane 3). 3.82 g of the expected product is obtained.
IR $CHCl_3$
>C=NH 3314 $cm^{-1}$
C≡N 2230 $cm^{-1}$
C=N 1678–1670–1876
C=S 1505–1495 $cm^{-1}$
Aromatics Stage C: 4-(4,4-bis(hydroxymethyl) 3-methyl 5-oxo 2-thioxo 1-imidazolidinyl) 2-(trifluoromethyl) benzonitrile 3.8 g of the product obtained in Stage B above is introduced into 38 ml of methanol and 19 ml of 2N hydrochloric acid, then the mixture is heated under reflux. After about 2 hours, it is poured into 200 ml of water and extracted with ether then with ethyl acetate. The organic phases are united and washed with salt water then the solvent is evaporated off. Purification is carried out on silica (eluant: $CH_2Cl_2$—MeOH (95–5)) then the product is dissolved in 30 ml of isopropyl ether under reflux, followed by filtration and partial concentration. After ice-cooling for about one hour and separating, 282 mg of expected product (yellow crystals) is obtained. M.p.=169° C.–170° C.

| | Microanalysis | | | | |
|---|---|---|---|---|---|
| | C | H | F | N | S |
| % calculated | 46.80 | 3.37 | 15.86 | 11.69 | 8.92 |
| % found | 46.8 | 3.3 | 15.9 | 11.5 | 9.0 |

IR Nujol
OH/NH 3410–3385 $cm^{-1}$
C≡N 2240 $cm^{-1}$
C=O 1720 $cm^{-1}$
Aromatics 1608–1580–1568 $cm^{-1}$
UV EtOH
Max 234 nm ε=17600
Max 256 nm ε=23200

EXAMPLE 22

4-(4,4-bis(1-oxopropoxy) methyl) 3-methyl 5-oxo 2-thioxo 1-imidazolidinyl) 2-(trifluoromethyl) benzonitrile 200 mg of the product of Example 21 is introduced into 2 ml of pyridine and 25 mg of 4-dimethylamino pyridine then 16 ml of propionic anhydride is added. After reaction for 25 minutes, the mixture is poured into 20 ml of sodium bicarbonate and extracted with methylene chloride, the organic phase is washed with salt water, dried, the solvent is evaporated off and distillation is carried out 3 times with 30 ml of toluene. Purification is carried out on silica (eluant: $Cl_2Cl_2$), then crystallization from ether and 239 mg of expected product (white crystals) is obtained. M.p.=117° C.–118° C.

| | Microanalysis | | | | |
|---|---|---|---|---|---|
| | C | H | F | N | S |
| % calculated | 50.95 | 4.27 | 12.09 | 8.91 | 6.80 |
| % found | 51.2 | 4.5 | 12.1 | 8.8 | 6.9 |

IR $CHCl_3$
>C=O 1755–1762 $cm^{-1}$
C≡N 2235 $cm^{-1}$
Aromatics and C=S 1615–1580–1504–1488 $cm^{-1}$
UV EtOH
Infl 236 nm ε=18800
Max 253 nm ε=22600
Infl 265 nm ε=18200

EXAMPLE 23

4-(4,4-bis(fluoromethyl) 3-methyl 5-oxo 2-thioxo 1-imidazolidinyl) 2-(trifluoromethyl) benzonitrile 1 ml of tetrahydrofuran is cooled down to –50° C. and 0.66 ml of diethylaminosulphide trifluoride is added then the solution, cooled down to a temperature of about –50° C., of 360 mg of the product of Example 21 in 4 ml of tetrahydrofuran is added drop by drop. The resultant mixture is heated to a temperature of about 30° C.

After about 30 minutes, the resultant mixture is poured drop by drop into 50 ml of a saturated aqueous solution of sodium bicarbonate, extraction is carried out with chloroform, the organic phase is washed with salt water and the solvent; is evaporated off. Purification is carried out on silica with $CH_2Cl_2$—cyclohexane (9–1) as eluant then the product is dissolved in 20 ml of isopropanol at a temperature of about 60° C. Filtration is carried out, followed by rinsing with 1 ml of isopropanol and concentration, ice-cooling for one hour and separating. 314 mg of expected product (white crystals) is obtained. M.p.=122° C.–123° C.

| | Microanalysis | | | | |
|---|---|---|---|---|---|
| | C | H | F | N | S |
| % calculated | 46.28 | 2.77 | 26.15 | 11.56 | 8.82 |
| % found | 46.3 | 2.7 | 25.7 | 11.25 | 8.8 |

IR $CHCl_3$
C≡N 2236 $cm^{-1}$
C=O 1763 $cm^{-1}$
Aromatics 1615–1580–1504–1487 $cm^{-1}$
UV EtOH
Infl 237 nm ε=20300
Max 250 nm ε=22000
Infl 266 nm ε=17100

EXAMPLE 24

4-(4,4-bis(hydroxymethyl) 3-methyl 2,5-dioxo 1-imidazolidinyl) 2-(trifluoromethyl) benzonitrile
1) Formation of the tetrahydropyranic ethers
360 mg of the product of Example 21 is introduced into 5 ml of tetrahydrofuran, 1 ml of 3,4-dihydro 2H pyran, and 15 mg of paratoluene sulphonic acid, $H_2O$.

After about 40 minutes, 10 ml of a saturated aqueous solution of sodium bicarbonate and 1 ml of triethylamine are poured into the mixture, extraction is carried out with chloroform, the extracts are washed with salt water, dried and the solvent is evaporated off.

Purification is carried out on silica (eluant: $CH_2Cl_2$—MeOH (93–7)) and 600 mg of expected product is obtained, used as it is for the following stage.

2) Transition to hydantoin 600 mg of the diether obtained in 1) is introduced into 4 ml of dimethylformamide and 55 mg of 50% sodium hydride is added, then after cessation of the release of hydrogen, 0.09 ml of methyl iodide is added. About 40 minutes afterwards, 110 mg of 50% sodium hydride, then 10 minutes afterwards 0.18 ml of methyl iodide are successively added. The reaction mixture is poured into 10 ml of ice-cooled water containing 1.3 g of monopotassium phosphate and extraction is carried out with ether. The organic phase is washed with salt water, dried and the solvent is evaporated off. Purification is carried out on silica (eluant: $CH_2Cl_2$—ethyl acetate (92.5–7.5)) and 370 mg of expected product is obtained, used as it is for the following stage.

3) Deprotection of the pvranic ethers 370 mg of the product obtained above in 2) is introduced into 4 ml of methanol and 2 ml of 2N hydrochloric acid then the solution is taken to 60° C. for about 2 hours.

The solution is then poured into 15 ml of salt water, drying is carried out, the solvent is evaporated off then the residue is dissolved in 20 ml of acetone and evaporated to dryness. Purification is carried out on silica (eluant: $CH_2Cl_2$—MeOH (92.5–7.5)) followed by recrystallization from acetone and 197 mg of expected product (white crystals) is obtained, M.p.=217° C.–218° C.

UV EtOH
Max 263 nm ε=14600
Infl 237, 278, 287 nm

EXAMPLE 25

4-(4,4-bis(hydroxymethyl) 3-methyl 5-imino 2thioxo 1-imidazolidinyl) 2-(trifluoromethyl) benzonitrile The operation is carried out as in Example 21 and at Stage C of the preparation of Example 21, 421 mg of expected product is obtained.

IR
C≡N 2230 $cm^{-1}$
C=N, C=S 1680–1614–1580–1510 $cm^{-1}$
Aromatics

EXAMPLE 26

4-(4,4-bis(hydroxymethyl)-2,5-dioxo-1-imidazolidinyl)-2-(trifluoromethyl)-benzonitrile Stage 1: 1,3 bis [(tetrahydro 2H pyran-2 yl) oxy] 2 propanone 9 g of 2,5-dihydroxy 1,4-dioxane 2,5-dimethanol is introduced into 60 ml of dioxane and the suspension is taken to about 70° C. for 15 minutes then returned to ambient temperature. 20 ml of 3,4-dihydro 2H-pyran and 300 mg of monohydrated paratoluene sulphonic acid are then added and the temperature is maintained at about 40° C. then the medium is left for 16 hours at ambient temperature.

The medium is then poured into a mixture of 300 ml of a saturated solution of sodium bicarbonate +10 ml of triethylamine and extraction is carried out with methylene chloride. The organic phase is washed with salt water, dried and the solvent is evaporated off.

After chromatography on silica (eluant: ethyl cycloacetate/triethylamine 8/2), 17 g of expected product is obtained (pale yellow syrup).

ANALYSES:
IR $CHCl_3$ ($cm^{-1}$)
Absence of OH
O=C 1736

Stage 2: 2-amino 3-((tetrahydro-2H-pyran-2-yl) oxy) 2(((tetrahydro-2H-pyran-2-yl) oxy) methyl) propanenitrile 5.6 g of the product obtained in Stage 1 above is introduced into 8 ml of ammonium hydroxide, the mixture is taken to about –5° C. and 1.58 g of ammonium chloride and 1.23 g of sodium cyanide are added successively and the resultant mixture is left to rise to ambient temperature over about 40 minutes then heated at 40° C.±5° C. under agitation for 16 hours. It is returned to ambient temperature and extracted with chloroform, the organic phase is washed with salt water, dried and the solvent is evaporated off.

After chromatography on silica (eluant: ethyl cycloacetate/triethylamine 3/7), 4.41 g of expected product (pale yellow syrup) is obtained.

ANALYSES:
IR $CHCl_3$ ($cm^{-1}$)
—CN 2235
NH2 3390–3317

Stage 3: 4-(5-imino-2-oxo-4,4-bis(((tetrahydro-2H-pyran-2-yl) oxy) methyl) 1-imidazolidinyl) 2-(trifluoromethyl) benzonitrile 570 mg of the product obtained in Stage 2 above is introduced into 5 ml of isopropyl ether and 0.28 ml of triethylamine and the mixture is taken to –30° C. then 2.32 g of a solution of the product obtained in the preparation of Example 7 of the European Patent Application EP 0.494.819 at 18.4% in 1,2-dichloroethane is added over one hour.

4 ml of methylene chloride is added then the reaction medium is left to return to ambient temperature, left for about 2 hours and the solvent is evaporated off. After purification on silica (eluant: methylene chloride/acetone 9/1), 700 mg of expected product is obtained.

ANALYSES:
IR $CHCl_3$ ($cm^{-1}$)
NH 3442–3317
—CN 2235
C=O 1757
C=N 1670
Aromatic 1614–1575–1505

Stage 4: 4-(4,4-bis(hydroxymethyl)-2,5-dioxo-1-imidazolidinyl)-2-(trifluoromethyl)-benzonitrile 300 mg of the product obtained in Stage 3 above is introduced into 3 ml of methanol and 1.5 ml of 2N hydrochloric acid and the mixture is taken to reflux for one hour 30 minutes.

It is returned to ambient temperature, poured into 5 ml of an aqueous solution of sodium bicarbonate, extracted with ethyl acetate then the extracts are washed with a saturated aqueous solution of sodium chloride, dried and the solvent is evaporated off.

5 ml of methanol is added and purification is carried out on silica (eluant: methylene chloride—methanol 9/1).

The product is taken up in 20 ml of isopropanol under reflux then concentration is carried out and 225 mg of expected product (white crystals) is obtained, M.p.=207° C.208° C.

ANALYSES:
IR NUJOL
OH/NH 3525–3365–3250 $cm^{-1}$
CN 2240 $cm^{-1}$
C=O 1778–1738 $cm^{-1}$
Aromatic 1618–1578–1506 $cm^{-1}$

EXAMPLE 27

4-(4,4-bis(fluoromethyl) 2,5-dioxo 3-methyl 1-imidazolidinyl) 2-(trifluoromethyl) benzonitrile The operation is carried out as indicated in Example 23 using 120 mg of the product obtained in Example 24. After chromatography on silica (eluant: $CH_2Cl_2$—ethyl acetate 99–1), 111 mg of expected product is obtained. M.p.=137° C.–138° C.
ANALYSES:
IR $CHCl_3$
$C\equiv N$ 2235 $cm^{-1}$
$C=O$ 1790–1735 $cm^{-1}$
Aromatic 1617–1580–1505 $cm^{-1}$

EXAMPLE 28

4-(2,5-dioxo 3-ethyl 4-(hydroxymethyl 4-methyl 1-imidazolidinyl) 2-(trifluoromethyl) benzonitrile The operation is carried out as indicated in Example 2, Stages 2 and 3, using 1.033 g of the tetrahydropyranic ether prepared in Stage 1 and 0.24 ml of ethyl iodide. After chromatography on silica (eluant: methylene chloride—ethyl acetate), 0.796 g of expected product is obtained which is recrystallized from isopropanol. M.p.=138° C.
ANALYSES:
IR $CHCl_3$
OH 3616 $cm^{-1}$
$C\equiv N$ 2236 $cm^{-1}$
$C=O$ 1779 (m)–1725 (F) $cm^{-1}$
Aromatic 1617–1506 $cm^{-1}$

EXAMPLE 29

3-(2,5-dioxo 3-ethyl 4-methyl 4-(2-methyl 1-oxopropoxy) methyl 1-imidazolidinyl) 2-(trifluoromethyl) benzonitrile The operation is carried out as in Example 22 using 280 mg of product obtained in Example 28, 2.5 ml of pyridine, 23 mg of dimethylaminopyridine and 0.16 ml of isobutyric anhydride. After extraction with ether, elimination of the solvents and chromatography on silica (eluant: methylene chloride—ethyl acetate 100–1), 321 mg of expected product is obtained. M.p.=85° C.
ANALYSES:
IR $CHCl_3$
$C\equiv N$ 2235 $cm^{-1}$
$C=O$ 1781 (m)–1728 (F) $cm^{-1}$
Aromatic 1615–1575–1505 $cm^{-1}$

EXAMPLE 30

Carbonate of (1-(4-cyano 3-(trifluoromethyl) phenyl) 2,5-dioxo 3-ethyl 4-methyl 4-imidazolidinyl) methyl and of 1-methylethyl The operation is carried out as in Example 22 using 376 mg of the product obtained in Example 28, 3.8 ml of pyridine, 25 mg of dimethylaminopyridine, and 2.2 ml of a toluene solution of isopropyl chloroformate (1M/l) is added at 0° C. After agitation for 30 minutes at 0° C. then for 3 hours at ambient temperature, 0.4 ml of the isopropyl chloroformate solution is added and agitation is continued at ambient temperature for 2 hours 30 minutes. The reaction medium is poured into 20 g of ice-cooled water, extracted with ether, the organic solution is washed with salt water, dried and the solvents are eliminated under reduced pressure. The residue is taken up in toluene, concentrated to dryness, the oil formed is left to crystallize and 422 mg of crude product is obtained which is chromatographed on silica (eluant: methylene chloride—ethyl acetate 100–2). 270 mg of expected product is obtained. M.p.=123° C.

ANALYSES:
IR $CHCl_3$
$C\equiv N$ 2235 $cm^{-1}$
$C=O$ 1782–1744–1729 $cm^{-1}$
Aromatic 1616–1578–1505 $cm^{-1}$

EXAMPLE 31

4-(4,4-bis(hydroxymethyl) 2,5-dioxo 3-(4-hydroxybutyl) 1-imidazolidinyl) 2-trifluoromethyl) benzonitrile.

1) Formation of the tetrahydropyranic ethers.

The operation is carried out as in Example 24 Stage 1, using 331 mg of the product obtained in Example 26. Extraction is carried out with methylene chloride, the extracts are washed with salt water, dried, the solvent is evaporated off and, after chromatography on silica (eluant: $CH_2Cl_2$—MeOH 9–1), 500 mg of expected product is obtained, used as it is for the following stage.

2) Hydroxyalkylation.

456 mg of the diether obtained above in 3 ml of dimethylsulphoxide is added drop by drop over 20 minutes to 52 mg of sodium hydride then 20 minutes after cessation of the release of hydrogen, 374 mg of trimethylsilyl-4-iodo-butanol is added. After 40 minutes of reaction, the medium is poured into 20 ml of water, extracted with ether, the organic phase is washed with salt water, dried and the solvent is evaporated off. 650 mg of crude product is obtained which is used as it is for the following stage.

3) Hydrolysis of the protective groups.

650 mg of the product obtained above is introduced into 7 ml of methanol and 3 ml of 2N hydrochloric acid then the solution is taken to 40° C. for about 40 minutes. It is poured into 20 ml of an aqueous solution of sodium bicarbonate, extracted with ethyl acetate, the extracts are washed with salt water, dried, the solvent is evaporated off. Purification is carried out on silica (eluant: $CH_2Cl_2$—MeOH 9–1) and 950 mg of expected product is obtained.
ANALYSES:
UV EtOH
Max. 237 nm $\epsilon$=8600
Max. 263 nm $\epsilon$=14000
Infl. 278 nm $\epsilon$=8400
Infl. 287 nm $\epsilon$=4200

EXAMPLE 32

4-(4,4-bis(hydroxymethyl) 2,5-dioxo 3-(2-fluoroethyl) 1-imidazolidinyl) 2-trifluoromethyl) benzonitrile.

1) Fluoroalkylation.

The operation is carried out as in Example 3 Stage a, starting with 5 g of the tetrahydropyranic diether prepared as indicated in Example 31 Stage 1, and 1.1 ml of 2-bromo 1-fluoroethane. 5.31 g of expected product is obtained.

2) Hydrolysis of the tetrahydropyranic ether.

The operation is carried out as in Example 3 Stage b starting with 550 mg of the product obtained above, 6 ml of methanol and 2 ml of 2N hydrochloric acid. After chromatography on silica (eluant: $CH_2Cl_2$—$Me_2CO$ 8–2), 351 mg of expected product is obtained. M.p.=138° C.–139° C.
ANALYSES:
IR NUJOL
OH/NH 3580–3505 $cm^{-1}$
$C\equiv N$ 2245 $cm^{-1}$
$C=O$ 1778–1716 $cm^{-1}$
Aromatic 1616–1580–1512 $cm^{-1}$
UV EtOH

EXAMPLE 33

4-(4,4-bis(fluoromethyl) 2,5-dioxo 3-(2-fluoroethyl) 1-imidazolidinyl) 2-trifluoromethyl) benzonitrile.

1 ml of tetrahydrofuran is cooled down to −50° C. under an inert atmosphere and 0.66 ml of diethylamino sulphide trifluoride is added drop by drop, then 375 mg of the product obtained in Example 32 in 4 ml of tetrahydrofuran is added over 5 minutes. The reaction medium is left to return to ambient temperature, maintained under agitation for one hour, poured into an ice-cooled aqueous solution of sodium bicarbonate, extraction is carried out with chloroform, the organic phase is washed with salt water, dried, the solvent is evaporated off, the residue is chromatographed on silica (eluant: $CH_2Cl_2$—cyclohexane 9–1) and 337 mg of expected product is obtained. M.p.=136–137° C.
ANALYSES:
IR $CHCl_3$
$C{\equiv}N$ 2235 $cm^{-1}$
$C{=}O$ 1787–1736 $cm^{-1}$
Aromatic 1617–1577–1505 $cm^{-1}$

EXAMPLE 34

4-(4,4-bis(2-methyl 1-oxopropoxy) methyl) 2,5-dioxo 3-(2-fluoroethyl) 1-imidazolidinyl) 2-trifluoromethyl) benzonitrile.

0.5 ml of isobutyric anhydride is added under an inert atmosphere to a solution containing 375 mg of the product obtained in Example 32, 4 ml of pyridine and 122 mg of dimethylamino-pyridine. Agitation is carried out for 30 minutes, the reaction medium is poured into 20 ml of a 50% aqueous solution of sodium bicarbonate, followed by drying and evaporating the solvent under reduced pressure. The residue is chromatographed on silica (eluant: $CH_2Cl_2$—AcOEt 95–5) and 457 mg of expected product is obtained. M.p.=71° C.–72° C.
ANALYSES:
IR $CHCl_3$
$C{\equiv}N$ 2236 $cm^{-1}$
$C{=}O$ 1789–1733 $cm^{-1}$
Aromatic 1616–150 $cm^{-1}$
UV EtOH
Max. 257 nm $\epsilon$=17000
Infl. 285 nm $\epsilon$=2600

EXAMPLE 35

Carbonate of bis (1-methylethyl) and (3-(4-cyano 3-(trifluoromethyl) phenyl) 2,4-dioxo 1-(2-fluoroethyl) 5-imidazolidinyl) bis (methylene) and ± racemic of carbonate of (3-(4-cyano 3-(trifluoromethyl) phenyl) 2,4-dioxo 1-(2-fluoroethyl) 5-(hydroxymethyl) 5-imidazolidinyl) methyl and of 1-methylethyl 375 mg of the product obtained in Example 32 in 4 ml of pyridine and 122 mg of 4-dimethylaminopyridine is cooled down to −4° C. under an argon atmosphere. 550 mg of isopropyl chloroformate is added drop by drop at −4° C. The reaction medium is left to return to ambient temperature, agitation is continued for 2 hours. The reaction being incomplete, 122 mg of dimethylaminopyridine and 2 ml of isopropyl chloroformate are added and the mixture is heated for 18 hours at 50° C. It is returned to ambient temperature, poured into salt water, extraction is carried out with ethyl acetate, the extracts are dried, the solvents are eliminated, and 570 mg of crude product is obtained which is purified by chromatography on silica (eluant: $CH_2Cl_2$—AcOEt 95–5), in order to obtain 275 mg of dicarbonate (M.p.=122° C.–123° C.) then (eluant: $CH_2Cl_2$—$Me_2CO$ 9–1), in order to obtain 156 mg of monocarbonate (M.p.=154° C.–155° C.).
ANALYSES:
. Dicarbonate
IR $CHCl_3$
$C{\equiv}N$ 2238 $cm^{-1}$
$C{=}O$ 1789–1749–1734 $cm^{-1}$
Aromatic 1615–1578–1505 $cm^{-1}$
UV EtOH
Max. 256 nm $\epsilon$=15400
Infl. 285 nm $\epsilon$=2500
. Monocarbonate
IR (Nujol)
OH/NH 3450 $cm^{-1}$
$C{\equiv}N$ 2250 $cm^{-1}$
$C{=}O$ 1789–1736 $cm^{-1}$
Aromatic 1616–1576–1506 $cm^{-1}$

EXAMPLE 36

Carbonate of bis (2-methylpropyl) and of (3-(4-cyano 3-(trifluoromethyl) phenyl) 2,4-dioxo 1-(2-fluoroethyl) 5-imidazolidinyl) bis (methylene)

375 mg of the product obtained in Example 32 in 4 ml of pyridine and 122 mg of 4-dimethylaminopyridine is cooled down to −4° C. under an argon atmosphere. 550 mg of isobutyl chloroformate is added drop by drop at −4° C. The medium is left to return to ambient temperature. After 40 minutes, the reaction medium is poured into water, washed with salt water, dried and the solvents are eliminated, the residue is chromatographed on silica (eluant: $CH_2Cl_2$—AcOEt 92.5–7.5) and 476 mg of expected product is obtained. M.p.=109°–110° C.
ANALYSES:
IR $CHCl_3$
$C{\equiv}N$ 2236 $cm^{-1}$
$C{=}O$ 1790–1754–1734 $cm^{-1}$
Aromatic 1615–1578–1505 $cm^{-1}$
UV EtOH
Max. 256 nm $\epsilon$=15500
Infl. 285 nm $\epsilon$=2700

EXAMPLE 37

Tablets were prepared having the following composition:

| | |
|---|---|
| Product of Example 3 | 100 mg |
| Excipient s.q. for a tablet made up to | 300 mg |

(Detail of the excipient: lactose, starch, talc, magnesium stearate).

EXAMPLE 38

Tablets were prepared having the following composition:

| | |
|---|---|
| Product of Example 26 | 100 mg |
| Excipient s.q. for a tablet made up to | 300 mg |

(Detail of the excipient: lactose, starch, talc, magnesium stearate).

Max. 260 nm $\epsilon$=15300
Infl. 280 nm $\epsilon$=3400

PHARMACOLOGICAL STUDY OF THE PRODUCTS OF THE INVENTION

1) Study of the affinity of the products of the invention for the androgen receptor Male Sprague Dawley EOPS rats weighing 180–200 g, castrated 24 hours previously, are sacrificed, the prostates are removed, weighed and homogenized at 0° C. using a Potter glass, in a buffered solution (10 mM Tris, 0.25M saccharose, 0.1 mM PMSF (phenylmethanesulphonylfluoride), 20 mM sodium molybdate, HCl pH 7.4) to which is added extemporaneously 2 mM of DTT (DL dithiothreitol), at the rate of 1 g of tissue per 8 ml of buffer.

The homogenate is then ultracentrifuged at 0° C., for 30 minutes at 209,000 g. Aliquots of the supernatant obtained (=cytosol), are incubated for 30 minutes and 24 hours at 0° C., with a constant concentration (T) of tritiated testosterone and in the presence of increasing concentrations (0 to $2500.10^{-9}M$), either of unlabelled testosterone, or of the products under test. The concentration of bound tritiated testosterone (B) is then measured in each incubate by the method of adsorption with carbon-dextran. Calculation of the relative bond affinity (RBA).

The following 2 curves are drawn: the percentage of the bound tritiated hormone B/T as a function of the logarithm of the concentration of the unlabelled reference hormone and B/T as a function of the logarithm of the concentration of the unlabelled product tested. The straight line of the equation $I_{50}=(B/Tmax+B/Tmin)/2$ is determined. B/Tmax=% of the bound tritiated hormone for an incubation of this tritiated hormone at the concentration (T). B/Tmin=% of the bound tritiated hormone for an incubation of this tritiated hormone at the concentration (T) in the presence of a large excess of unlabelled hormone $(2500.10^{-9}M)$.

The intersections of the straight line $I_{50}$ and the curves enable the concentrations of the unlabelled reference hormone (CH) and of the unlabelled tested product (CX) which inhibit by 50% the binding of the tritiated hormone on the receptor to be evaluated. The relative bond affinity (RBA) of the tested product is determined by the equation RBA=100 (CH)/(CX).

The following results, expressed in RBA, are obtained. Reference product (Testosterone): 100

| Product of Examples | Incubation: 24 hours |
|---|---|
| 3 | 6 |
| 6 | 16 |
| 26 | 4 |

2) Determination of the androgen or anti-androgen activity of the products of the invention using dosage of ornithine decarboxylase (ODC).

Treatment protocol 6-week old male SWISS mice, castrated 24 hours previously, receive, by oral or percutaneous route, the products being studied (suspension in methyl cellulose at 0.5% or in solution in ethanol), simultaneously with a subcutaneous injection of testosterone propionate 3 mg/kg (solution in corn oil) in order to determine the antiandrogen activity. The agonistic activity is determined in the absence of testosterone propionate.

Testosterone propionate is administered in a volume of 10 ml/kg.

20 hours after the treatments, the animals are sacrificed, the kidneys are removed, then homogenized at 0° C., using a teflon glass grinder in 10 volumes of Tris-HCl 50 mM (pH 7.4) buffer containing 250 µM of pyridoxal phosphate, 0.1 mM EDTA, and 5 mM of dithiothreitol. The homogenate is then centrifuged at 209,000 g for 30 minutes.

Dosage principle

At 37° C., renal ornithine decarboxylase converts an isotopic mixture of unlabelled ornithine and tritiated ornithine into unlabelled putrescine and tritiated putrescine.

The putrescine is then collected on selective ion-exchange papers. After drying, the excess unconverted tritiated and unlabelled ornithine is eliminated by washing 3 times with 0.1M of ammonium hydroxide. The papers are dried, then the radioactivity is counted after addition of scintillating Aqualite.

The results are expressed as fmoles $(10^{-15}M)$ of tritiated putrescine formed/hour/mg of proteins.

The results are expressed as % of inhibition of the ODC of the controls receiving only testosterone propionate. Test: the products are administered by percutaneous route at 1.5 mg/kg in a volume of 10 µl.

| Products of Examples | Test |
|---|---|
| 3 | 47 |
| 6 | 84 |

Conclusion: The tests indicated above show that the tested products of the invention possess a strong anti-androgen activity.

We claim:

1. A compound in all possible racemic, enantiomeric and diastereoisomer forms of the formula

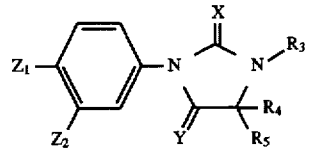

wherein Y is —O—, $Z_2$ is —$CF_3$, $Z_1$ is —CN or —$NO_2$, X is —O— or —S—, $R_3$ is hydrogen or alkyl of 1 to 4 carbon atoms optionally substituted by at least one halogen or —CN and $R_4$ and $R_5$ are individually alkyl of 1 to 4 carbon atoms optionally substituted with a member of the group consisting of halogen, —OH, esterified or esterified or protected hydroxy and phenylthio optionally substituted by halogen or —OH, and wherein at least one of $R_4$ and $R_5$ is substituted.

2. A compound of a) of claim 1 selected from the group consisting of 2-(trifluoromethyl)-4-(4-(hydroxymethyl)-4-methyl-2,5-dioxo-1-imidazolidinyl)-benzonitrile, 4-(3,4-dimethyl)-4-(hydroxymethyl)-5-oxo-2-thioxo-1-imidazolidinyl)-2-(triflouromethyl)-benzonitrile, 2-(trifluoromethyl)-4-(4-(hydroxymethyl)-3,4-dimethyl-2,5-dioxo-1-imidazolidinyl)-benzonitrile, 4-(2,5-dioxo-3-(2-fluoroethyl)-4-(hydroxymethyl)-4-methyl-1-imidazolidinyl)-2-(trifluoromethyl)-benzonitrile, 1,5-dimethyl-5-(hydroxymethyl)-3-(4-nitro-3-(trifluoromethyl)-phenyl)-2,4-imidazolidinedione and 4-(4,4-bis (hydroxymethyl)-2,5-dioxo-1-imidazolidinyl)-2-(trifluoromethyl)-benzonitrile.

3. A compound of b) of claim 1 selected from the group consisting of 4-(4-(fluoromethyl)-(3,4-dimethyl)-2,5-dioxo-1-imidazolidinyl)-2-(trifluoromethyl)-benzonitrile, 4-(3,4-dimethyl)-4-(fluoromethyl)-5-oxo-2-thioxo-1-imidazolidinyl)-2-(trifluoromethyl)-benzonitrile, 4-(2,5-dioxo-3-(2-fluoroethyl)-4-(fluoromethyl)-4-methyl-1-imidazolidinyl)-2-(triflouromethyl)-benzonitrile, 4-(2,4- dioxo-1,3-diazaspiro(4.4)nonan-3-yl)-2-(trifluoromethyl)-benzonitrile, 4-(2,4-dioxo-1-(2-fluoroethyl)-1,3-diazaspiro (4.4) nonan-3-yl-2-(triflouromethyl)-benzonitrile, 1,5-dimethyl-5-(fluoromethyl)-3-(4-nitro-3-(trifluoromethyl)-phenyl-2,4-imidazolidinedione, 3-(4-cyano-3-(trifluoromethyl)-phenyl)-2,4-dioxo-5-(fluoromethyl)-5-methyl-1-imidazolidinacetonitrile and 4-(4,4-bis-(fluoromethyl)-3-methyl-5-oxo-2-thioxo-1-imidazolidinyl-2-(trifluoromethyl)-benzonitrile.

4. A method of inducing antiandrogenic activity in warm-blooded animals comprising administering to warm-blooded animals an antiandrogenically effective amount of a compound of claim 1.

5. A method of inducing antiandrogenic activity in warm-blooded animals comprising administering to warm-blooded animals an antiandrogenically effective amount of a compound of claim 2.

6. A method of inducing antiandrogenic activity in warm-blooded animals comprising administering to warm-blooded animals an antiandrogenically effective amount of a compound of claim 3.

* * * * *